United States Patent
Yamagata et al.

(10) Patent No.: US 11,439,692 B2
(45) Date of Patent: Sep. 13, 2022

(54) METHOD OF TREATING DISEASES ASSOCIATED WITH MYD88 PATHWAYS USING CRISPR-GNDM SYSTEM

(71) Applicant: Modalis Therapeutics Corporation, Chuo-ku (JP)

(72) Inventors: Tetsuya Yamagata, Cambridge, MA (US); Yuanbo Qin, Cambridge, MA (US); Iain Robert Thompson, Cambridge, MA (US); Haruhiko Morita, Chuo-ku (JP)

(73) Assignee: Modalis Therapeutics Corporation, Chuo-ku (JP)

(*) Notice: Subject to any disclaimer, the term of this patent is extended or adjusted under 35 U.S.C. 154(b) by 53 days.

(21) Appl. No.: 16/614,145

(22) PCT Filed: May 17, 2018

(86) PCT No.: PCT/JP2018/019913
§ 371 (c)(1),
(2) Date: Nov. 15, 2019

(87) PCT Pub. No.: WO2018/212361
PCT Pub. Date: Nov. 22, 2018

(65) Prior Publication Data
US 2021/0260170 A1 Aug. 26, 2021

Related U.S. Application Data

(60) Provisional application No. 62/507,340, filed on May 17, 2017.

(51) Int. Cl.
| | |
|---|---|
| A61K 48/00 | (2006.01) |
| C12N 15/11 | (2006.01) |
| A61K 38/46 | (2006.01) |
| A61P 35/00 | (2006.01) |
| A61K 31/7105 | (2006.01) |
| C07K 14/47 | (2006.01) |
| C12N 9/22 | (2006.01) |

(52) U.S. Cl.
CPC ........ *A61K 38/465* (2013.01); *A61K 31/7105* (2013.01); *A61P 35/00* (2018.01); *C07K 14/47* (2013.01); *C12N 9/22* (2013.01); *C12N 15/11* (2013.01)

(58) Field of Classification Search
CPC .................. A61K 48/00; C12N 15/11
See application file for complete search history.

(56) References Cited

U.S. PATENT DOCUMENTS

| | | |
|---|---|---|
| 2010/0092486 A1 | 4/2010 | Kandimalla et al. |
| 2016/0046961 A1 | 2/2016 | Jinek et al. |

FOREIGN PATENT DOCUMENTS

| | | |
|---|---|---|
| WO | WO 2010/017436 A2 | 2/2010 |
| WO | WO 2013/176772 A1 | 11/2013 |

OTHER PUBLICATIONS

Moghadam et al. 2020; Synthetic immunomodulation with a CRISPR super-repressor in vivo. Nature Cell Biology. vol. 22, pp. 1143-1154.*
International Search Report dated Aug. 21, 2018 in PCT/JP2018/019913 filed on May 17, 2018.
Thakore et al., "CRISPR/Cas9-Based Transcriptional Repressors for Control of Human Gene Expression," Molecular Therapy, vol. 22, Supplement 1, May 2014, pp. S214-S215.
Miura et al., "Toll-Like Receptor 9 Promotes Steatohepatitis by Induction of Interleukin-1β in Mice," Gastroenterology, vol. 139, No. 1, 2010, pp. 323-334 and 334.e1-334.e7.
Caner et al., "MYD88 Expression and L265P Mutation in Mature B-Cell Non-Hodgkin Lymphomas," Genetic Testing and Molecular Biomarkers, vol. 19, No. 7, 2015, pp. 372-378.
Radzisheuskaya et al., "Optimizing sgRNA position markedly improves the efficiency of CRISPR/dCas9-mediated transcriptional repression," Nucleic Acids Research, vol. 44, No. 18, e141, Jun. 2016, pp. 1-13.
Deguine et al., "MyD88: a central player in innate immune signaling," F1000Prime Reports, vol. 6, No. 97, Nov. 2014, pp. 1-7.
Drexler et al., "The role of Toll-like receptors in chronic inflammation," Elsevier, The International Journal of Biochemistry & Cell Biology, vol. 42, 2010, pp. 506-518, doi:10.1016/j.biocel.2009.10.009.
Yang et al., "A mutation in MYD88 (L265P) supports the survival of lymphoplasmacytic cells by activation of Bruton tyrosine kinase in Waldenstrom macroglobulinemia," Blood, vol. 122, No. 7, Aug. 2013, pp. 1222-1232.
Loiarro et al., "Targeting the Toll-like Receptor/Interleukin 1 Receptor Pathway in Human Diseases: Rational Design of MyD88 Inhibitors," IWWM 2012 Proceedings, Clinical Lymphoma, Myeloma & Leukemia, vol. 13, No. 2, Apr. 2013, pp. 222-226.

\* cited by examiner

*Primary Examiner* — Karen Cochrane Carlson
(74) *Attorney, Agent, or Firm* — Oblon, McClelland, Maier & Neustadt, L.L.P.

(57) ABSTRACT

The present invention provides a method of treating a disease associated with activated MYD88 signaling in a subject, including suppressing MYD88 expression in a subject by targeting an expression regulatory region of MYD88 gene by using a CRISPR-Guide Nucleotide Directed Modulation (GNDM), without affecting the expression of an adjacent ACAA1 gene. Also, provided is a CRISPR-GNDM system for suppressing MYD88, including expression comprising (a) a protein selected from the group consisting of dCas9 or dCpf1, a fusion protein of dCas9 or dCpf1 and Kruppel associated box (KRAB) and (b) a guide RNA (gRNA) targeting an expression regulatory region of MYD88 gene.

17 Claims, 3 Drawing Sheets
Specification includes a Sequence Listing.

about 5.9 kb MYD88 specific regulatory region

SEQUENCE LISTING

```
<160> NUMBER OF SEQ ID NOS: 69

<210> SEQ ID NO 1
<211> LENGTH: 20
<212> TYPE: DNA
<213> ORGANISM: Homo Sapiens

<400> SEQUENCE: 1
ggcgatgttt ggaaactcgg                                              20

<210> SEQ ID NO 2
<211> LENGTH: 20
<212> TYPE: DNA
<213> ORGANISM: Homo Sapiens

<400> SEQUENCE: 2
tgtcaccttc acctagactg                                              20

<210> SEQ ID NO 3
<211> LENGTH: 20
<212> TYPE: DNA
<213> ORGANISM: Homo Sapiens

<400> SEQUENCE: 3
cttataacac tgtgccctag                                              20

<210> SEQ ID NO 4
<211> LENGTH: 20
<212> TYPE: DNA
<213> ORGANISM: Homo Sapiens
```

```
<400> SEQUENCE: 4
gataggagaa aaccgccctg                                          20

<210> SEQ ID NO 5
<211> LENGTH: 20
<212> TYPE: DNA
<213> ORGANISM: Homo Sapiens

<400> SEQUENCE: 5
ctttacgggt gtctgcaaag                                          20

<210> SEQ ID NO 6
<211> LENGTH: 20
<212> TYPE: DNA
<213> ORGANISM: Homo Sapiens

<400> SEQUENCE: 6
attcacgtcc ttgagaaccg                                          20

<210> SEQ ID NO 7
<211> LENGTH: 20
<212> TYPE: DNA
<213> ORGANISM: Homo Sapiens

<400> SEQUENCE: 7
gcctcacctt gaagccgccg                                          20

<210> SEQ ID NO 8
<211> LENGTH: 20
<212> TYPE: DNA
<213> ORGANISM: Homo Sapiens

<400> SEQUENCE: 8
aatcggccgg acccctcagg                                          20

<210> SEQ ID NO 9
<211> LENGTH: 20
<212> TYPE: DNA
<213> ORGANISM: Homo Sapiens

<400> SEQUENCE: 9
accacaagga gagtcggcct                                          20

<210> SEQ ID NO 10
<211> LENGTH: 20
<212> TYPE: DNA
<213> ORGANISM: Homo Sapiens

<400> SEQUENCE: 10
cctatagagg gcttggtagg                                          20

<210> SEQ ID NO 11
<211> LENGTH: 20
<212> TYPE: DNA
<213> ORGANISM: Homo Sapiens

<400> SEQUENCE: 11
ccccgcccag aaatgcagac                                          20

<210> SEQ ID NO 12
<211> LENGTH: 20
<212> TYPE: DNA
```

```
<213> ORGANISM: Homo Sapiens

<400> SEQUENCE: 12
caggaccgct tactgcttgg                                         20

<210> SEQ ID NO 13
<211> LENGTH: 20
<212> TYPE: DNA
<213> ORGANISM: Homo Sapiens

<400> SEQUENCE: 13
gcccgagtcc tgctccgacg                                         20

<210> SEQ ID NO 14
<211> LENGTH: 20
<212> TYPE: DNA
<213> ORGANISM: Homo Sapiens

<400> SEQUENCE: 14
agagaggtac catgtatccg                                         20

<210> SEQ ID NO 15
<211> LENGTH: 20
<212> TYPE: DNA
<213> ORGANISM: Homo Sapiens

<400> SEQUENCE: 15
ccctgctatt gggagtcaag                                         20

<210> SEQ ID NO 16
<211> LENGTH: 20
<212> TYPE: DNA
<213> ORGANISM: Homo Sapiens

<400> SEQUENCE: 16
cgtttcccac tcccacctcg                                         20

<210> SEQ ID NO 17
<211> LENGTH: 20
<212> TYPE: DNA
<213> ORGANISM: Homo Sapiens

<400> SEQUENCE: 17
gaacccctca gattcctccg                                         20

<210> SEQ ID NO 18
<211> LENGTH: 20
<212> TYPE: DNA
<213> ORGANISM: Homo Sapiens

<400> SEQUENCE: 18
catcaccaga ccctcgaggg                                         20

<210> SEQ ID NO 19
<211> LENGTH: 20
<212> TYPE: DNA
<213> ORGANISM: Homo Sapiens

<400> SEQUENCE: 19
tggagccccg agcaaaagtg                                         20

<210> SEQ ID NO 20
<211> LENGTH: 20
```

```
<212> TYPE: DNA
<213> ORGANISM: Homo Sapiens

<400> SEQUENCE: 20
tcggaaagcg aaagccggcg                                              20

<210> SEQ ID NO 21
<211> LENGTH: 20
<212> TYPE: DNA
<213> ORGANISM: Homo Sapiens

<400> SEQUENCE: 21
ctgctctcaa catgcgagtg                                              20

<210> SEQ ID NO 22
<211> LENGTH: 20
<212> TYPE: DNA
<213> ORGANISM: Homo Sapiens

<400> SEQUENCE: 22
gtcggcctac agaggcgcca                                              20

<210> SEQ ID NO 23
<211> LENGTH: 20
<212> TYPE: DNA
<213> ORGANISM: Homo Sapiens

<400> SEQUENCE: 23
gtgaggaggc tgactttccg                                              20

<210> SEQ ID NO 24
<211> LENGTH: 20
<212> TYPE: DNA
<213> ORGANISM: Homo Sapiens

<400> SEQUENCE: 24
gactggagaa aggtccggat                                              20

<210> SEQ ID NO 25
<211> LENGTH: 20
<212> TYPE: DNA
<213> ORGANISM: Homo Sapiens

<400> SEQUENCE: 25
acaggtgggg cgattgacag                                              20

<210> SEQ ID NO 26
<211> LENGTH: 20
<212> TYPE: DNA
<213> ORGANISM: Homo Sapiens

<400> SEQUENCE: 26
aatcactgca ccataaccag                                              20

<210> SEQ ID NO 27
<211> LENGTH: 20
<212> TYPE: DNA
<213> ORGANISM: Homo Sapiens

<400> SEQUENCE: 27
attcttagga tccctaggaa                                              20

<210> SEQ ID NO 28
```

```
<211> LENGTH: 20
<212> TYPE: DNA
<213> ORGANISM: Homo Sapiens

<400> SEQUENCE: 28
tggtgccacg cgaagctcaa                                               20

<210> SEQ ID NO 29
<211> LENGTH: 20
<212> TYPE: DNA
<213> ORGANISM: Homo Sapiens

<400> SEQUENCE: 29
agtattggac ccttacccag                                               20

<210> SEQ ID NO 30
<211> LENGTH: 20
<212> TYPE: DNA
<213> ORGANISM: Homo Sapiens

<400> SEQUENCE: 30
aggttggcta gaaggccacg                                               20

<210> SEQ ID NO 31
<211> LENGTH: 20
<212> TYPE: DNA
<213> ORGANISM: Homo Sapiens

<400> SEQUENCE: 31
tgccaggggt acttagatgg                                               20

<210> SEQ ID NO 32
<211> LENGTH: 20
<212> TYPE: DNA
<213> ORGANISM: Homo Sapiens

<400> SEQUENCE: 32
cacagccact ggttccatgc                                               20

<210> SEQ ID NO 33
<211> LENGTH: 20
<212> TYPE: DNA
<213> ORGANISM: Homo Sapiens

<400> SEQUENCE: 33
aggaaataag gctcaaggtg                                               20

<210> SEQ ID NO 34
<211> LENGTH: 20
<212> TYPE: DNA
<213> ORGANISM: Homo Sapiens

<400> SEQUENCE: 34
ggagctgaga gcatgaccac                                               20

<210> SEQ ID NO 35
<211> LENGTH: 20
<212> TYPE: DNA
<213> ORGANISM: Homo Sapiens

<400> SEQUENCE: 35
cacaggttca gtcctaagca                                               20
```

```
<210> SEQ ID NO 36
<211> LENGTH: 20
<212> TYPE: DNA
<213> ORGANISM: Homo Sapiens

<400> SEQUENCE: 36
actacgattc tgtgtgacga                                               20

<210> SEQ ID NO 37
<211> LENGTH: 20
<212> TYPE: DNA
<213> ORGANISM: Homo Sapiens

<400> SEQUENCE: 37
ttggggtata tactcccaag                                               20

<210> SEQ ID NO 38
<211> LENGTH: 20
<212> TYPE: DNA
<213> ORGANISM: Homo Sapiens

<400> SEQUENCE: 38
tactagccaa acgaccagaa                                               20

<210> SEQ ID NO 39
<211> LENGTH: 20
<212> TYPE: DNA
<213> ORGANISM: Homo Sapiens

<400> SEQUENCE: 39
accccaagaa atccacacca                                               20

<210> SEQ ID NO 40
<211> LENGTH: 20
<212> TYPE: DNA
<213> ORGANISM: Homo Sapiens

<400> SEQUENCE: 40
gagtcaaggc acttaaagca                                               20

<210> SEQ ID NO 41
<211> LENGTH: 24
<212> TYPE: DNA
<213> ORGANISM: Homo Sapiens

<400> SEQUENCE: 41
gagggtcgct cgcgtctgtt cgca                                          24

<210> SEQ ID NO 42
<211> LENGTH: 24
<212> TYPE: DNA
<213> ORGANISM: Homo Sapiens

<400> SEQUENCE: 42
ggagggtcgc tcgcgtctgt tcgc                                          24

<210> SEQ ID NO 43
<211> LENGTH: 24
<212> TYPE: DNA
<213> ORGANISM: Homo Sapiens

<400> SEQUENCE: 43
tgggcgggga ttcgtaaaga taca                                          24
```

```
<210> SEQ ID NO 44
<211> LENGTH: 24
<212> TYPE: DNA
<213> ORGANISM: Homo Sapiens

<400> SEQUENCE: 44
cgaatccccg cccagaaatg caga                                            24

<210> SEQ ID NO 45
<211> LENGTH: 24
<212> TYPE: DNA
<213> ORGANISM: Homo Sapiens

<400> SEQUENCE: 45
ggggtcaggt ctcgggtttg gcta                                            24

<210> SEQ ID NO 46
<211> LENGTH: 24
<212> TYPE: DNA
<213> ORGANISM: Homo Sapiens

<400> SEQUENCE: 46
gtagccaaac ccgagacctg accc                                            24

<210> SEQ ID NO 47
<211> LENGTH: 24
<212> TYPE: DNA
<213> ORGANISM: Homo Sapiens

<400> SEQUENCE: 47
tagccaaacc cgagacctga cccc                                            24

<210> SEQ ID NO 48
<211> LENGTH: 24
<212> TYPE: DNA
<213> ORGANISM: Homo Sapiens

<400> SEQUENCE: 48 ggtccccag ctcgggtact ggga                                             24

<210> SEQ ID NO 49
<211> LENGTH: 24
<212> TYPE: DNA
<213> ORGANISM: Homo Sapiens

<400> SEQUENCE: 49
ggcttccggg ctggccggga gaac                                            24

<210> SEQ ID NO 50
<211> LENGTH: 24
<212> TYPE: DNA
<213> ORGANISM: Homo Sapiens

<400> SEQUENCE: 50
acagacatgc ggggtgtgac aagc                                            24

<210> SEQ ID NO 51
<211> LENGTH: 24
<212> TYPE: DNA
<213> ORGANISM: Homo Sapiens

<400> SEQUENCE: 51
ctacaacccc cgaaggaggg tcgt                                            24
```

<210> SEQ ID NO 52
<211> LENGTH: 24
<212> TYPE: DNA
<213> ORGANISM: Homo Sapiens

<400> SEQUENCE: 52
gagatctgga gaggtccacg gcac                                              24

<210> SEQ ID NO 53
<211> LENGTH: 24
<212> TYPE: DNA
<213> ORGANISM: Homo Sapiens

<400> SEQUENCE: 53
cgagaagcgc cgccctgccc taca                                              24

<210> SEQ ID NO 54
<211> LENGTH: 24
<212> TYPE: DNA
<213> ORGANISM: Homo Sapiens

<400> SEQUENCE: 54
gctttccgag aagcgccgcc ctgc                                              24

<210> SEQ ID NO 55
<211> LENGTH: 24
<212> TYPE: DNA
<213> ORGANISM: Homo Sapiens

<400> SEQUENCE: 55
tcctgcggca cccgccccgc cccg                                              24

<210> SEQ ID NO 56
<211> LENGTH: 24
<212> TYPE: DNA
<213> ORGANISM: Homo Sapiens

<400> SEQUENCE: 56
cgcggcctca gcatcctgtc tccc                                              24

<210> SEQ ID NO 57
<211> LENGTH: 24
<212> TYPE: DNA
<213> ORGANISM: Homo Sapiens

<400> SEQUENCE: 57
ctgcctcggg ggcccgaaga agcc                                              24

<210> SEQ ID NO 58
<211> LENGTH: 24
<212> TYPE: DNA
<213> ORGANISM: Homo Sapiens

<400> SEQUENCE: 58
ggcaatcctc ctctgtgggg aaga                                              24

<210> SEQ ID NO 59
<211> LENGTH: 24
<212> TYPE: DNA
<213> ORGANISM: Homo Sapiens

<400> SEQUENCE: 59
caggtggccg ctgtagacag cagt                                                    24

<210> SEQ ID NO 60
<211> LENGTH: 24
<212> TYPE: DNA
<213> ORGANISM: Homo Sapiens

<400> SEQUENCE: 60
gcccagccca aggagacccc acct                                                    24

<210> SEQ ID NO 61
<211> LENGTH: 12
<212> TYPE: RNA
<213> ORGANISM: Streptococcus pyogenes
<220> FEATURE:
<221> NAME/KEY: misc_structure
<222> LOCATION: (1)..(12)
<223> OTHER INFORMATION: crRNA direct repeat sequence

<400> SEQUENCE: 61
guuuuagagc ua                                                                 12

<210> SEQ ID NO 62
<211> LENGTH: 14
<212> TYPE: RNA
<213> ORGANISM: Streptococcus pyogenes
<220> FEATURE:
<221> NAME/KEY: misc_structure
<222> LOCATION: (1)..(14)
<223> OTHER INFORMATION: tracrRNA anti-repeat region

<400> SEQUENCE: 62
uagcaaguua aaau                                                               14

<210> SEQ ID NO 63
<211> LENGTH: 48
<212> TYPE: RNA
<213> ORGANISM: Streptococcus pyogenes
<220> FEATURE:
<221> NAME/KEY: misc_structure
<222> LOCATION: (1)..(48)
<223> OTHER INFORMATION: tracrRNA subsequent stem-loop 1, linker,
      stem-loop 2 and stem-loop 3 regions

<400> SEQUENCE: 63
aaggcuaguc cguuaucaac uugaaaaagu ggcaccgagu cggugcuu                          48

<210> SEQ ID NO 64
<211> LENGTH: 19
<212> TYPE: RNA
<213> ORGANISM: Francisella novicida
<220> FEATURE:
<221> NAME/KEY: misc_structure
<222> LOCATION: (1)..(19)
<223> OTHER INFORMATION: crRNA direct repeat sequence

<400> SEQUENCE: 64
aauuucuacu cuuguagau                                                          19

<210> SEQ ID NO 65
<211> LENGTH: 7352
<212> TYPE: DNA
<213> ORGANISM: Homo sapiens

<400> SEQUENCE: 65
ctttacgggt gtctgcaaag aggccttcct cttttactaa tactcctcag cacagaccct            60

```
ttacgggtgt cgggctgggg gactgtaagg tctttcccct cccactaggc catatctcag    120
acaatctcag tgggggaaaa cctggacaat acccaggctt tcttgggcag aggtccctgc    180
ggcctttcgc agtgcactgt gtacctggtt aatcgagaat ggagaatggc gatgactttt    240
accaagcata ctgcctgcaa acaaatggtt aacaagccac atcctgcaca gccctaaatc    300
cctcaaacct tgattcaata cagcacatgt ttctgtgagc acagggttgg ggctaaggct    360
acagattaac agcatctcaa ggcagaaaaa ttttcttag tacagatcaa aatgagtttt     420
cttctgtctt ccttttctac acagacacag taacagtctg atctctcttc ctttccccca    480
cactgccgca ctccccttgc cgagatagtg aaaatagtaa tcaataaata ctagggaac    540 tcggagaccg atgccggtca cctgggccca ctctacactt tgtctctgcg tcttatttct    600
tttctcagtc tctcctccca tctgacgaga ataccaca ggtgtgaagg ggcaggaccc     660
cttcaaaggt caaggccatg gaggttcccc cagtgaaaat tcgggcggg gaggtgagga     720 gagctctgga cgaacggaag aacgggaag gcccagcgca gggcctgagt ggttcgctca     780
ccgacacaga tgtcccccag ctgttccggc ctcagattca cgtccttgag aaccgcggtc    840
atgactgccg agagaagctc gtcgggggtg tgtcctgca gcagaaagag cagccgcagt     900 gaccccccact cccccatgcc cacccaggg agacaaagcg accacagctg ggtgcggagc    960
tgcctccggc gtccaggata accaaacata cgaaccggac cccagcccgc gccggcgtct   1020
tcccacactc ggcgcccaga ccctcgggcc tcaccttgaa gccgccgcgg cccgcccggc   1080
agatggccgt gcgccgcccg tgcaccacca ccacgtccgc ggccgaggcc tgcggggcac   1140
cgctcaggca aggcgcggcc tgcggcatcc agccggaatc ggccggaccc ctcaggtggc   1200
ccagcactac ctgcagcctc tgcattgcgc aggtcaaccc tgcagaccag ccaccagtcc   1260
gggaactgac cgcggagtta acagacagcc gtccgcacac gcgcagaacc acatctcagc   1320
ctccaaggcc tcaactccgc ccacagctct gcgaacagac gcgagcgacc ctccaaaagt   1380
cccgtccacc tccagcctca gccaaccaca aggagagtcg gcctgggaac ccgcccctcc   1440
ccgccaccgc ctaccaagcc ctctatagga gggcccacag gcaccgccca gccgagcttt   1500
ccactcaatg ccccgcctac cttggcctac cgcagccaac cagaaggtgt atctttacga   1560
atccccgccc agaaatgcag accggaagtc tttccacctt ttgtagccaa acccgagacc   1620
tgacccccaa atccctgtct cctgcccgca gccaaacgga aggctgggca gccaggaccg   1680
cttactgctt gggggctgga gatggaagcc gaggctctaa ttcctctacc cacttcctag   1740
gaggctctgc tatccctccg gtcccagtac ccgagctggg ggacctaaat acttccgaga   1800
cgcccgagtc ctgctccgac gtggttgggc tttcccattc tttcgagaag acagggaatt   1860
tgggcttccg ggctggccgg gagaacagat tttacagaca tgcggggtgt gacaagctct   1920
ctaactggag aatgaacatt tcacactttt accagtttta cacccaattg gaatgatttt   1980
attagtgccc atttccgtg ctaggctggg gtctccacca aggcagagag gtaccatgta    2040
tccggggagc ctgcgacacc cttgacactt agtagatgat caataagtac ttgtcgaatg   2100
agtaaatgaa tgaaccaggg ctccccaggt caggactgtg tccctaaacc taagggcaa    2160 ggccacgtgc ccccttgact cccaatagca gggccatgtc ttcacctgag acctggaga    2220 gtagtgctgg gctttccaca gacaccaaag gacagggtgc cttgtgctcc ccaacctagt   2280
gtcatgacgt cccccaaccat ttcgagggca gggccacggc atgcctcagg ctccagaagg   2340
cagctgtccg tttcccactc ccacctcggg gagcacagca ggggtcttcc catacccta    2400 ctggcaggat tgcgtgttcc ccagagacag tggagggcag agctggtgcc ttcccacttg   2460
```

```
tcccctcctc gccatcctcg agggcaggac cgtatgaacc cctcagattc ctccgtggaa   2520
gaactgtggc tccaccagat cccaaaaagc aaggcccgtt tcctacaacc cccgaaggag   2580
ggtcgtcctc actccgccgc caacctacta gcaccatcac cagaccctcg agggcggtgc   2640
cgtggacctc tccagatctc aaaaggcaga ttcctacttc ttacgccccc cacatcaccc   2700
gcctcgagac ctcaagggta gaggtgggca ccccgcctc cgcacttttg ctcggggctc    2760
cagattgtag ggcagggcgg cgcttctcgg aaagcgaaag ccggcggggc ggggcgggtg   2820
ccgcaggaga aagaggaagc gctggcagac aatgcgaccc gaccgcgctg aggctccagg   2880
accgcccgcc atggctgcag gaggtccccgg cgcggggtct gcggcccggg tctcctccac   2940 atcctcccctt cccctggctg ctctcaacat gcgagtgcgg cgccgcctgt ctctgttctt   3000
gaacgtgcgg acacaggtgg cggccgactg gaccgcgctg gcggaggaga tggactttga   3060
gtacttggag atccggcaac tggagacaca agcggacccc actggcaggc tgctggacgc   3120
ctggcaggga cgccctggcg cctctgtagg ccgactgctc gagctgctta ccaagctggg   3180
ccgcgacgac gtgctgctgg agctgggacc cagcattggt gaggacgtcc ccttcctggc   3240
ctcgtacctg gggggtgagg aggctgactt tccgcgcct cagcatcctg tctcccatgg    3300
agagacccca tttcctgcct cgggggcccg aagaagcctg cagagggaga accatgcggg   3360
tcccgttcct tcttaataac cggtcgcggt tattaagaag gactgagaa aggtccggat    3420 aggcggagat gggaaggaag cagcttaggc agaggctttc aggtagggcc aggagtcaga   3480
atcaggcttc tgtgggggca tctggctgt ttcaagtaga gcaacaggac aggtggggcg    3540
attgacagtg gactgtctta gaaacctcaa gtcctgggga aatgcagccc ttctttctac   3600
tcactggcac ttacataata tacatgcata ggcgttggat acagccgccc acagacaggc   3660
acaccttgct gagttggaat cactgcacca taaccagtgg gtctcctgag cctttctggc   3720
atgcccagcc ccttgctcac atctgccctg gatcccagaa gaagcagacc taccttggta   3780
ccattcttag gatccctagg aagggacaga gatacaaacc tgactttgat ggccttccag   3840
aaagccagaa caccactgac atcccttttgg gtcagttaga gccagtggga gctcaacttc   3900
tcagagccgt tgagcttcgc gtggcaccag tgaactgggg aagccctcta gaacaaccca   3960
gccagaggag gtgggacagc ggctggatcc tgactgtggg taaagaggta ggcactccca   4020
gggaggctgc tttactctgt ctcttcccca cagaggagga ttgccaaaag tatatcttga   4080
agcagcagca ggaggaggct gagaagcctt tacaggtggc cgctgtagac agcagtgtcc   4140 cacgacagc agagctggcg ggcatcacca cacttgatga cccctgggt aagggtccaa     4200 tactgttccc atgggacagg tggaatagga cattgtggtg ttaagagcat gggtgtttga   4260
agcagatggg ctgtgagacc ttgggcaagt cacttaatct ttctgagcct cagtttcctc   4320
acctaagaaa tggagataat agtcctacct ctggattgct gtgagatgct catgaaataa   4380
tgtctgtctc gtggttaatc cagagcttag ccccctgaggg actcatcttt cctctcctgg   4440
aaagggcact ttctctgagg agtatcatct tgggaagggt gcagggccca gggttgccta   4500
ggcaggggac tcttggctgg atccctccca agccttccca tggagctctg accaccaccc   4560
ttgtgctctg cacccaggggc atatgcctga gcgtttcgat gccttcatct gctattgccc   4620
cagcgacatc cagtttgtgc aggagatgat ccggcaactg aacagacaa actatcgact    4680 gaagttgtgt gtgtctgacc gcgatgtcct gcctggcacc tgtgtctggt ctattgctag   4740
tgagctcatc gaaaagaggt tggctagaag gccacggggt gggtgcgtgg atgcatgaag   4800
```

```
ccctgccctg gggtccagat actgggcatc tcctcctagc tgtgcactgt ccagcctggg    4860
cacagtgggc ccttcctgaa gctattccca ggggatatgc tgaactaagt tgccacagga    4920
cctgcagcct gcccactctc ccctaggtgc cgccggatgg tggtggttgt ctctgatgat    4980
tacctgcaga gcaaggaatg tgacttccag accaaatttg cactcagcct ctctccaggt    5040
aagctcaacc ctgctctggc aagagaatga gggaatgtgt aggtggggcc tctggattgt    5100
cagccttccc tccccaagga ctgtggatgc agtaccaaag aactgctgaa gatctctgca    5160
cacctgagca tgtgtgcatg tgtgtgcctt tttgtgtgag tgaatgtgtg ccaggggtac    5220
ttagatgggg gatggctgtt gttaaccctg gggttgaaga ctgggcttgt cccaccatgg    5280
ggcaagggcc tgatgccagc atggcacccc ttggcttgca ggtgcccatc agaagcgact    5340
gatccccatc aagtacaagg caatgaagaa agagttcccc agcatcctga ggttcatcac    5400
tgtctgcgac tacaccaacc cctgcaccaa atcttggttc tggactcgcc ttgccaaggc    5460
cttgtccctg ccctgaagac tgttctgagg ccctgggtgt gtgtgtatct gtctgcctgt    5520
ccatgtactt ctgccctgcc tcctcctttc gttgtaggag gaatctgtgc tctacttacc    5580
tctcaattcc tggagatgcc aacttcacag acacgtctgc agcagctgga catcacattt    5640
catgtcctgc atggaaccag tggctgtgag tggcatgtcc acttgctgga ttatcagcca    5700
ggacactata gaacaggacc agctgagact aagaaggacc agcagagcca gctcagctct    5760
gagccattca cacatcttca ccctcagttt cctcacttga ggagtgggat ggggagaaca    5820
gagagtagct gtgtttgaat ccctgtagga aatggtgaag catagctctg ggtctcctgg    5880
gggagaccag gcttggctgc gggagagctg gctgttgctg gactacatgc tggccactgc    5940
tgtgaccacg acactgctgg ggcagcttct tccacagtga tgcctactga tgcttcagtg    6000
cctctgcaca ccgcccattc cacttcctcc ttccccacag ggcaggtggg gaagcagttt    6060
ggcccagccc aaggagaccc caccttgagc cttatttcct aatgggtcca cctctcatct    6120
gcatctttca cacctcccag cttctgccca accttcagca gtgacaagtc cccaagagac    6180
tcgcctgagc agcttgggct gcttttcatt tccacctgtc aggatgcctg tggtcatgct    6240
ctcagctcca cctggcatga aagggatcc tggcctctgg catattcatc aagtatgagt    6300
tctggggatg agtcactgta atgatgtgag cagggagcct tcctccctgg ccacctgca    6360 gagagctttc ccaccaactt tgtaccttga ttgccttaca agttatttg tttacaaaca    6420 gcgaccatat aaaagcctcc tgccccaaag cttgtgggca catgggcaca tacagactca    6480
catacagaca cacacatata tgtacagaca tgtactctca cacacacagg caccagcata    6540
cacacgtttt tctaggtaca gctcccagga acagctaggt gggaaagtcc catcactgag    6600
ggagcctaac catgtccctg aacaaaaatt gggcactcat ctattccttt tctcttgtgt    6660
ccctactcat tgaaaccaaa ctctggaaag gacccaatgt accagtattt atacctctaa    6720
tgaagcacag agagaggaag agagctgctt aaactcacac aacaatgaac tgcagacaca    6780
gctgttctct ccctctctcc ttcccagagc aatttatact ttaccctcag gctgtcctct    6840
ggggagaagg tgccatggtc ttaggtgtct gtgccccagg acagaccta ggaccctaaa    6900 tccaatagaa aatgcatatc tttgctccac tttcagccag gctggagcaa ggtacctttt    6960
cttaggatct tgggagggaa tggatgcccc tctctgcatg atcttgttga ggcatttagc    7020
tgccatgcac ctgtccccct ttaatactgg gcattttaaa gccatctcaa gaggcatctt    7080
ctacatgttt tgtacgcatt aaaataattt caaagatatc tgagaaaagc cgatatttgc    7140
cattcttcct atatcctgga atatatcttg catcctgagt ttataataat aaataatatt    7200
```

```
ctaccttgga aacttgtgtg tgtgttgagt ggaagaggtt tggaagcagt aatgtgggta    7260
agagaagctg gtccactggg tgggttccag cctggatttg cacgggcttc ctgaaagct    7320 gggccccctc ctcacaggtt cagtcctaag ca                                  7352
```

<210> SEQ ID NO 66
<211> LENGTH: 1367
<212> TYPE: PRT
<213> ORGANISM: Streptococcus pyogenes

<400> SEQUENCE: 66

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
```

-continued

```
                340                 345                 350
Gln Ser Lys Asn Gly Tyr Ala Gly Tyr Ile Asp Gly Gly Ala Ser Gln
        355                 360                 365
Glu Glu Phe Tyr Lys Phe Ile Lys Pro Ile Leu Glu Lys Met Asp Gly
        370                 375                 380
Thr Glu Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
                420                 425                 430
Lys Asp Asn Arg Glu Lys Ile Glu Lys Ile Leu Thr Phe Arg Ile Pro
                435                 440                 445
Tyr Tyr Val Gly Pro Leu Ala Arg Gly Asn Ser Arg Phe Ala Trp Met
        450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
                500                 505                 510
Leu Tyr Glu Tyr Phe Thr Val Tyr Asn Glu Leu Thr Lys Val Lys Tyr
        515                 520                 525
Val Thr Glu Gly Met Arg Lys Pro Ala Phe Leu Ser Gly Glu Gln Lys
        530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
                580                 585                 590
Tyr His Asp Leu Leu Lys Ile Ile Lys Asp Lys Asp Phe Leu Asp Asn
        595                 600                 605
Glu Glu Asn Glu Asp Ile Leu Glu Asp Ile Val Leu Thr Leu Thr Leu
        610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
                645                 650                 655
Gly Trp Gly Arg Leu Ser Arg Lys Leu Ile Asn Gly Ile Arg Asp Lys
        660                 665                 670
Gln Ser Gly Lys Thr Ile Leu Asp Phe Leu Lys Ser Asp Gly Phe Ala
        675                 680                 685
Asn Arg Asn Phe Met Gln Leu Ile His Asp Asp Ser Leu Thr Phe Lys
        690                 695                 700
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
                740                 745                 750
His Lys Pro Glu Asn Ile Val Ile Glu Met Ala Arg Glu Asn Gln Thr
        755                 760                 765
```

-continued

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Ser Asp Lys Leu Ile Ala Arg Lys Lys Asp Trp Asp Pro Lys
            1115                1120                1125

Lys Tyr Gly Gly Phe Asp Ser Pro Thr Val Ala Tyr Ser Val Leu
            1130                1135                1140

Val Val Ala Lys Val Glu Lys Gly Lys Ser Lys Lys Leu Lys Ser
            1145                1150                1155

Val Lys Glu Leu Leu Gly Ile Thr Ile Met Glu Arg Ser Ser Phe
            1160                1165                1170

```
Glu  Lys  Asn  Pro  Ile  Asp  Phe  Leu  Glu  Ala  Lys  Gly  Tyr  Lys  Glu
     1175                1180                1185

Val  Lys  Lys  Asp  Leu  Ile  Ile  Lys  Leu  Pro  Lys  Tyr  Ser  Leu  Phe
     1190                1195                1200

Glu  Leu  Glu  Asn  Gly  Arg  Lys  Arg  Met  Leu  Ala  Ser  Ala  Gly  Glu
     1205                1210                1215

Leu  Gln  Lys  Gly  Asn  Glu  Leu  Ala  Leu  Pro  Ser  Lys  Tyr  Val  Asn
     1220                1225                1230

Phe  Leu  Tyr  Leu  Ala  Ser  His  Tyr  Glu  Lys  Leu  Lys  Gly  Ser  Pro
     1235                1240                1245

Glu  Asp  Asn  Glu  Gln  Lys  Gln  Leu  Phe  Val  Glu  Gln  His  Lys  His
     1250                1255                1260

Tyr  Leu  Asp  Glu  Ile  Ile  Glu  Gln  Ile  Ser  Glu  Phe  Ser  Lys  Arg
     1265                1270                1275

Val  Ile  Leu  Ala  Asp  Ala  Asn  Leu  Asp  Lys  Val  Leu  Ser  Ala  Tyr
     1280                1285                1290

Asn  Lys  His  Arg  Asp  Lys  Pro  Ile  Arg  Glu  Gln  Ala  Glu  Asn  Ile
     1295                1300                1305

Ile  His  Leu  Phe  Thr  Leu  Thr  Asn  Leu  Gly  Ala  Pro  Ala  Ala  Phe
     1310                1315                1320

Lys  Tyr  Phe  Asp  Thr  Thr  Ile  Asp  Arg  Lys  Arg  Tyr  Thr  Ser  Thr
     1325                1330                1335

Lys  Glu  Val  Leu  Asp  Ala  Thr  Leu  Ile  His  Gln  Ser  Ile  Thr  Gly
     1340                1345                1350

Leu  Tyr  Glu  Thr  Arg  Ile  Asp  Leu  Ser  Gln  Leu  Gly  Gly  Asp
     1355                1360                1365
```

<210> SEQ ID NO 67
<211> LENGTH: 9
<212> TYPE: PRT
<213> ORGANISM: Artificial Sequence
<220> FEATURE:
<223> OTHER INFORMATION: HA tag

<400> SEQUENCE: 67

```
Tyr  Pro  Tyr  Asp  Val  Pro  Asp  Tyr  Ala
1                   5
```

<210> SEQ ID NO 68
<211> LENGTH: 7
<212> TYPE: PRT
<213> ORGANISM: Artificial Sequence
<220> FEATURE:
<223> OTHER INFORMATION: nuclear localization signal

<400> SEQUENCE: 68

```
Pro  Lys  Lys  Lys  Arg  Lys  Val
1                   5
```

<210> SEQ ID NO 69
<211> LENGTH: 1396
<212> TYPE: PRT
<213> ORGANISM: Artificial Sequence
<220> FEATURE:
<223> OTHER INFORMATION: HA-NLS-dCas9-NLS

<400> SEQUENCE: 69

```
Met  Tyr  Pro  Tyr  Asp  Val  Pro  Asp  Tyr  Ala  Ser  Pro  Lys  Lys  Arg
1                   5                   10                  15

Lys  Val  Glu  Ala  Ser  Asp  Lys  Lys  Tyr  Ser  Ile  Gly  Leu  Ala  Ile  Gly
```

```
                20                  25                  30
Thr Asn Ser Val Gly Trp Ala Val Ile Thr Asp Glu Tyr Lys Val Pro
            35                  40                  45
Ser Lys Lys Phe Lys Val Leu Gly Asn Thr Asp Arg His Ser Ile Lys
        50                  55                  60
Lys Asn Leu Ile Gly Ala Leu Leu Phe Asp Ser Gly Glu Thr Ala Glu
65                  70                  75                  80
Ala Thr Arg Leu Lys Arg Thr Ala Arg Arg Tyr Thr Arg Arg Lys
                85                  90                  95
Asn Arg Ile Cys Tyr Leu Gln Glu Ile Phe Ser Asn Glu Met Ala Lys
            100                 105                 110
Val Asp Asp Ser Phe Phe His Arg Leu Glu Glu Ser Phe Leu Val Glu
            115                 120                 125
Glu Asp Lys Lys His Glu Arg His Pro Ile Phe Gly Asn Ile Val Asp
        130                 135                 140
Glu Val Ala Tyr His Glu Lys Tyr Pro Thr Ile Tyr His Leu Arg Lys
145                 150                 155                 160
Lys Leu Val Asp Ser Thr Asp Lys Ala Asp Leu Arg Leu Ile Tyr Leu
                165                 170                 175
Ala Leu Ala His Met Ile Lys Phe Arg Gly His Phe Leu Ile Glu Gly
            180                 185                 190
Asp Leu Asn Pro Asp Asn Ser Asp Val Asp Lys Leu Phe Ile Gln Leu
            195                 200                 205
Val Gln Thr Tyr Asn Gln Leu Phe Glu Glu Asn Pro Ile Asn Ala Ser
        210                 215                 220
Gly Val Asp Ala Lys Ala Ile Leu Ser Ala Arg Leu Ser Lys Ser Arg
225                 230                 235                 240
Arg Leu Glu Asn Leu Ile Ala Gln Leu Pro Gly Glu Lys Lys Asn Gly
                245                 250                 255
Leu Phe Gly Asn Leu Ile Ala Leu Ser Leu Gly Leu Thr Pro Asn Phe
            260                 265                 270
Lys Ser Asn Phe Asp Leu Ala Glu Asp Ala Lys Leu Gln Leu Ser Lys
            275                 280                 285
Asp Thr Tyr Asp Asp Asp Leu Asp Asn Leu Leu Ala Gln Ile Gly Asp
        290                 295                 300
Gln Tyr Ala Asp Leu Phe Leu Ala Ala Lys Asn Leu Ser Asp Ala Ile
305                 310                 315                 320
Leu Leu Ser Asp Ile Leu Arg Val Asn Thr Glu Ile Thr Lys Ala Pro
                325                 330                 335
Leu Ser Ala Ser Met Ile Lys Arg Tyr Asp Glu His His Gln Asp Leu
            340                 345                 350
Thr Leu Leu Lys Ala Leu Val Arg Gln Gln Leu Pro Glu Lys Tyr Lys
            355                 360                 365
Glu Ile Phe Phe Asp Gln Ser Lys Asn Gly Tyr Ala Gly Tyr Ile Asp
        370                 375                 380
Gly Gly Ala Ser Gln Glu Glu Phe Tyr Lys Phe Ile Lys Pro Ile Leu
385                 390                 395                 400
Glu Lys Met Asp Gly Thr Glu Glu Leu Leu Val Lys Leu Asn Arg Glu
                405                 410                 415
Asp Leu Leu Arg Lys Gln Arg Thr Phe Asp Asn Gly Ser Ile Pro His
            420                 425                 430
Gln Ile His Leu Gly Glu Leu His Ala Ile Leu Arg Arg Gln Glu Asp
            435                 440                 445
```

```
Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
        515                 520                 525

Pro Lys His Ser Leu Leu Tyr Glu Tyr Phe Thr Val Tyr Asn Glu Leu
    530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
        595                 600                 605

Ala Ser Leu Gly Thr Tyr His Asp Leu Leu Lys Ile Ile Lys Asp Lys
    610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
            660                 665                 670

Arg Arg Arg Tyr Thr Gly Trp Gly Arg Leu Ser Arg Lys Leu Ile Asn
        675                 680                 685

Gly Ile Arg Asp Lys Gln Ser Gly Lys Thr Ile Leu Asp Phe Leu Lys
    690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                725                 730                 735

Gly Asp Ser Leu His Glu His Ile Ala Asn Leu Ala Gly Ser Pro Ala
            740                 745                 750

Ile Lys Lys Gly Ile Leu Gln Thr Val Lys Val Val Asp Glu Leu Val
    755                 760                 765

Lys Val Met Gly Arg His Lys Pro Glu Asn Ile Val Ile Glu Met Ala
770                 775                 780

Arg Glu Asn Gln Thr Thr Gln Lys Gly Gln Lys Asn Ser Arg Glu Arg
                790                 795                 800
785

Met Lys Arg Ile Glu Glu Gly Ile Lys Glu Leu Gly Ser Gln Ile Leu
            805                 810                 815

Lys Glu His Pro Val Glu Asn Thr Gln Leu Gln Asn Glu Lys Leu Tyr
    820                 825                 830

Leu Tyr Tyr Leu Gln Asn Gly Arg Asp Met Tyr Val Asp Gln Glu Leu
    835                 840                 845

Asp Ile Asn Arg Leu Ser Asp Tyr Asp Val Asp Ala Ile Val Pro Gln
850                 855                 860
```

```
Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
            885                 890                 895

Lys Lys Met Lys Asn Tyr Trp Arg Gln Leu Leu Asn Ala Lys Leu Ile
        900                 905                 910

Thr Gln Arg Lys Phe Asp Asn Leu Thr Lys Ala Glu Arg Gly Gly Leu
            915                 920                 925

Ser Glu Leu Asp Lys Ala Gly Phe Ile Lys Arg Gln Leu Val Glu Thr
        930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
        980                 985                 990

Tyr Lys Val Arg Glu Ile Asn Asn Tyr His His Ala His Asp Ala Tyr
        995                 1000                1005

Leu Asn Ala Val Val Gly Thr Ala Leu Ile Lys Lys Tyr Pro Lys
    1010                1015                1020

Leu Glu Ser Glu Phe Val Tyr Gly Asp Tyr Lys Val Tyr Asp Val
    1025                1030                1035

Arg Lys Met Ile Ala Lys Ser Glu Gln Glu Ile Gly Lys Ala Thr
    1040                1045                1050

Ala Lys Tyr Phe Phe Tyr Ser Asn Ile Met Asn Phe Phe Lys Thr
    1055                1060                1065

Glu Ile Thr Leu Ala Asn Gly Glu Ile Arg Lys Arg Pro Leu Ile
    1070                1075                1080

Glu Thr Asn Gly Glu Thr Gly Glu Ile Val Trp Asp Lys Gly Arg
    1085                1090                1095

Asp Phe Ala Thr Val Arg Lys Val Leu Ser Met Pro Gln Val Asn
    1100                1105                1110

Ile Val Lys Lys Thr Glu Val Gln Thr Gly Gly Phe Ser Lys Glu
    1115                1120                1125

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
    1190                1195                1200

Ala Lys Gly Tyr Lys Glu Val Lys Lys Asp Leu Ile Ile Lys Leu
    1205                1210                1215

Pro Lys Tyr Ser Leu Phe Glu Leu Glu Asn Gly Arg Lys Arg Met
    1220                1225                1230

Leu Ala Ser Ala Gly Glu Leu Gln Lys Gly Asn Glu Leu Ala Leu
    1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
```

-continued

```
                    1265                1270                1275
Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320

Glu Gln Ala Glu Asn Ile Ile His Leu Phe Thr Leu Thr Asn Leu
    1325                1330                1335

Gly Ala Pro Ala Ala Phe Lys Tyr Phe Asp Thr Thr Ile Asp Arg
    1340                1345                1350

Lys Arg Tyr Thr Ser Thr Lys Glu Val Leu Asp Ala Thr Leu Ile
    1355                1360                1365

His Gln Ser Ile Thr Gly Leu Tyr Glu Thr Arg Ile Asp Leu Ser
    1370                1375                1380

Gln Leu Gly Gly Asp Ser Pro Lys Lys Lys Arg Lys Val
    1385                1390                1395
```

METHOD OF TREATING DISEASES ASSOCIATED WITH MYD88 PATHWAYS USING CRISPR-GNDM SYSTEM

TECHNICAL FIELD OF THE INVENTION

The present invention relates to a CRISPR-Guide Nucleotide Guided Modulation (GNDM) system for targeting MYD88 gene and suppressing its expression, and a method of treating disease associated with activated MYD88 signaling such as NASH, inflammatory diseases, autoimmune diseases and hematological malignancies by using the CRISPR-GNDM system.

BACKGROUND OF THE INVENTION

MYD88 is the critical adaptor for inflammatory signaling pathways downstream of members of the Toll-like receptor (TLR) and interleukin-1 (IL-1) receptor families. MYD88 links IL-1 receptor (IL-1R) and TLR family members to IL-1R-associated kinase (IRAK) family kinases via homotypic protein-protein interaction. Activation of IRAK family kinases leads to a variety of functional outputs, including the activation of nuclear factor-kappa B (NFκB), mitogen-activated protein kinases, and activator protein 1, making MYD88 a central node of inflammatory pathways (F1000Prime Rep. 2014 4; 6:97-104). MYD88 signaling plays an essential role in the activation of the innate and adaptive immune system by inducing the production of pro-inflammatory cytokines and activation of antigen presenting cells. Continuous activation or dysregulation on MYD88 signaling contributes to the pathogenesis of various autoimmune, infectious, and chronic inflammation diseases, including nonalcoholic steatohepatitis (NASH) (*Int J Biochem Cell Biol;* 42:506-518, 2010).

Development of NASH involves the innate immune system and is mediated by Kupffer cells and hepatic stellate cells (HSCs). TLR2, 4, 9 and IL-1R on these cell types play important role in the development and progression of NASH, and deletion of MYD88 has reduced steatohepatitis and fibrosis in the mouse model of NASH (Gastroenterology; 139:323-334, 2010). Thus, MYD88 plays a critical role in the development of NASH.

In cancers, a highly recurrent somatic mutation of MYD88(L265P) in Waldenstrom macroglobulinemia (WM) patients has been identified. More than 90% of WM or lymphoplasmacytic lymphoma (LPL) patients expressed MYD88 L265P. In addition, MYD88 L265P has also been reported in other B cell tumors such as ABC-type diffuse large B-cell lymphoma (DLBCL), primary central nervous system lymphoma, mucosa-associated lymphoid tissue lymphoma, and chronic lymphocytic leukemia (Blood, 122; 1222-1232, 2013).

Given its central role in the TLR/IL-1R signaling pathway leading to inflammatory responses and cell proliferation, interfering with the function of MYD88 is likely to represent a suitable approach for therapeutic treatment of diseases in which these receptors are involved. However, MYD88 has no catalytic activity, making it difficult to target via small molecule approaches. There have been attempts to interfere its homodimerization by a low-molecular drug discovery approaches (Clinical Lymphoma, Myeloma & Leukemia, 2152-2650, 2013). However, to date, there is no effective therapeutic agent for targeting MYD88.

SUMMARY OF THE INVENTION

The present inventors found that diseases associated with the activation of MYD88 including NASH, inflammatory diseases and hematological malignancies can be treated by suppressing MYD88 expression in the subject by targeting an expression regulatory region of the MYD88 gene by using a CRISPR-GNDM system. To be specific, the present inventors found that the MYD88 gene expression can be efficiently and selectively suppressed by targeting a specific expression regulatory region in and around the MYD88 gene to recruit cleavage activities inactivated CRISPR effector proteins such as dCas9 and dCpf1 proteins to said region.

Accordingly, the present invention provides:

[1] A method of treating a disease associated with MYD88 activation in a subject, comprising suppressing MYD88 expression in the subject by targeting an expression regulatory region of MYD88 gene using a CRISPR-GNDM system.

[2] The method of [1] above, wherein the MYD88 expression is suppressed without affecting the expression of an adjacent ACAA1 gene.

[3] The method of [1] or [2] above, wherein the disease is selected from the group consisting of an inflammatory disease, an autoimmune disease, an infectious disease and a cancer.

[4] The method of [1] or [2] above, wherein the disease is NASH.

[5] The method of [1] or [2] above, wherein the disease is a hematological malignancy.

[6] A CRISPR-GNDM system for suppressing MYD88 expression comprising (a) a protein selected from the group consisting of dCas9 or dCpf1, a fusion protein of dCas9 or dCpf1 and Kruppel associated box (KRAB) or other transcription repressor, and a fusion protein of dCas9 or dCpf1 and SunTag bound with KRAB or other transcription repressor, and (b) a guide nucleotide (gN) targeting an expression regulatory region of MYD88 gene.

[7] The CRISPR-GNDM system of [6] above, wherein the protein of (a) is selected from the group consisting of dCas9 or dCpf1, and a fusion protein of dCas9 or dCpf1 and Kruppel associated box (KRAB).

[8] The CRIPR-GNDM system of [6] or [7] above, wherein the expression regulatory region is a region having the nucleotide sequence shown by SEQ ID NO: 65.

[9] The CRISPR-GNDM system of [6] or [7] above, wherein the expression regulatory region is a region having the nucleotide sequence at positions 1,405-7,352 of SEQ ID NO: 65.

[10] The CRIPR-GNDM system of any one of [6]-[8] above, wherein the gN comprises a nucleotide sequence represented by any one of SEQ ID NOs:5 to 35.

[11] The CRIPR-GNDM system of any one of [6]-[9] above, wherein the gN comprises a nucleotide sequence represented by any one of SEQ ID NOs:9 to 35.

[12] The method of any one of [1]-[5] above, characterized in using the CRISPR-GNDM system of any one of [6]-[11] above.

The present invention can provide an effective therapeutic means for NASH by intercepting the chronic pro-inflammatory signaling mediated through MYD88 for which no known drugs are available.

DETAILED DESCRIPTION OF THE INVENTION

Figure 1A:
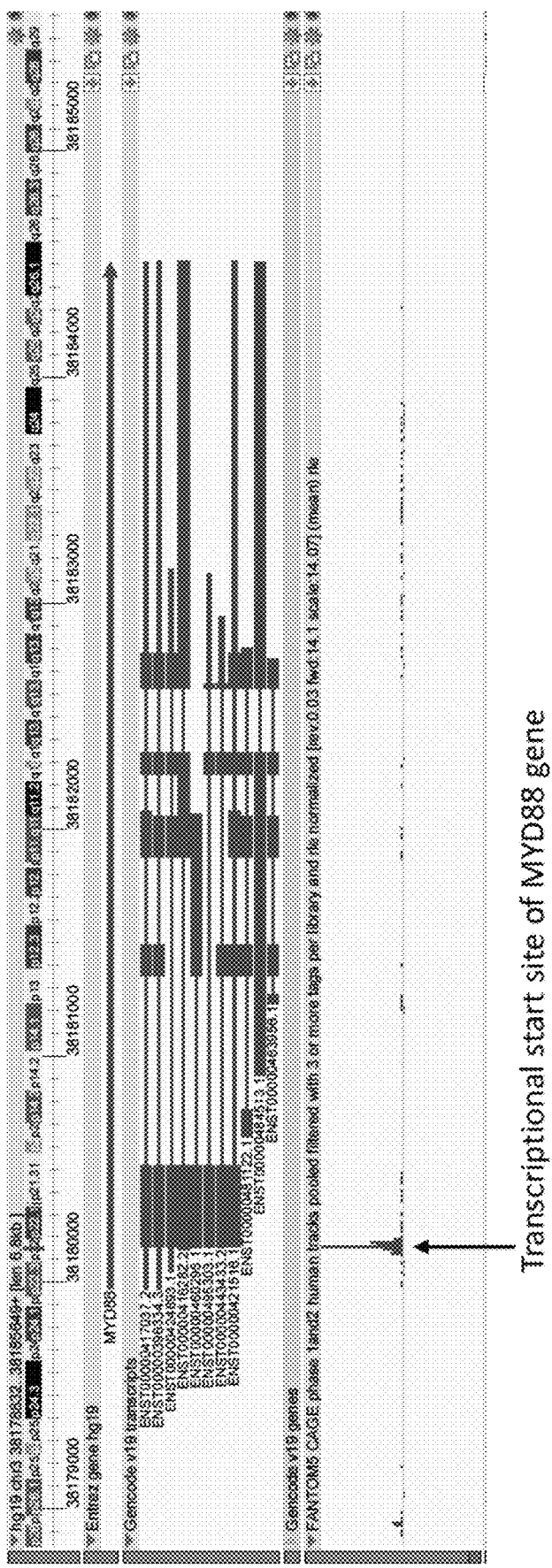
FIG. 1A shows the human MYD88 locus and a predicted transcript start site (TSS).

As used herein, the singular forms "a", "an" and "the" are intended to include both the singular and plural forms, unless the language explicitly indicates otherwise with words like "only," "single," and/or "one." It will be further understood that the terms "comprises", "comprising,", "includes" and/or "including", when used herein, specify the presence of stated features, steps, operations, elements, ideas, and/or components, but do not themselves preclude the presence or addition of one or more other features, steps, operations, elements, components, ideas, and/or groups thereof.

The present invention provides a method of treating a disease associated with activated MYD88 pathway and/or expression in a subject, comprising suppressing MYD88 expression in the subject by targeting a defined region of MYD88 gene using a CRISPR-Guide Nucleotide Directed Modulation (GNDM) system (hereinafter also referred to as "the method of the present invention").

1. Treatment Method of the Present Invention
<<Diseases Caused by the Activation of MYD88 Pathways>>

The present invention can be applicable to treat diseases caused by the activation of MYD88 pathways, which include, for example, inflammatory diseases (e.g. Chronic inflammatory conditions): nonalcoholic steatohepatitis (NASH), chronic hepatitis, primary biliary cirrhosis (PBS), inflammatory bowel diseases (IBD), atherosclerosis, liver cirrhosis, lung fibrosis, myelofibrosis; Autoimmune diseases: Systemic lupus erythematosus (SLE), Rheumatoid arthritis (RA), Multiple Sclerosis (MS), Sjogren's syndrome (SS), systemic cutaneous sclerosis (SCS); Infectious disease: viral infection, bacterial infection, tuberculosis, sepsis; Ischemic reperfusion injuries: transplantation graft rejections, Cancers: hematological malignancies (e.g. Waldenstrom macroglobulinemia (WM), lymphoplasmacytic lymphoma (LPL), ABC-type diffuse large B-cell lymphoma (DLBCL), primary central nervous system (CNS) lymphoma, mucosa-associated lymphoid tissue lymphoma (MALT), chronic lymphocytic leukemia (CLL), hemophagocytosis), pancreatic cancer, colorectal cancer, lung cancer.

<<CRISPR-GNDM System>>

According to the present invention, the expression of normal and mutated MYD88 genes can be sufficiently suppressed by recruiting a mutant Cas9 or Cpf1 that lacks double-stranded DNA break (DSB) activity (hereinafter also referred to as "dCas9" or "dCpf1", or collectively "dCas9/dCpf1") to an expression regulatory region of MYD88 gene, using CRISPR-GNDM system. The "expression regulatory region of MYD88 gene" as described herein may be any region of MYD88 gene as long as the expression of MYD88 gene can be suppressed as a result that dCas9/dCpf1 (and/or a transcription repressor bound therewith) is recruited thereto. Such region includes, but not limited to, the promoter, promoter-proximal and enhancer regions of MYD88 gene. As shown in the below-mentioned Examples, MYD88 gene expression can be suppressed, namely, selective suppression of MYD88 gene expression is possible, without affecting the expression of an ACAA1 gene adjacent to MYD88 gene, by setting a specific expression regulatory region having the nucleotide sequence shown by SEQ ID NO: 65, which corresponds to positions 38,135,811 to 38,143,162 of human chromosome 3 (CM000665) of MYD88 gene, as a target. As described herein, "without affecting the expression" means that, as compared to introduction of gRNA along into the cell without using a CRISPR effector protein, the relative average expression level of ACAA1 gene does not substantially change, which concretely means that the relative expression level is not more than 2-fold (e.g., not more than 1.6-fold, not more than 1.5-fold, not more than 1.4-fold, not more than 1.3-fold, not more than 1.2-fold, not more than 1.1-fold), and not less than 0.5-fold (e.g., not less than 0.6-fold, not less than 0.7-fold, not less than 0.8-fold, not less than 0.9-fold).

Recruiting the "dCas9/dCpf1" to the expression regulatory region of MYD88 gene is carried out by introducing a guide nucleotide (gN) that targets said region into a diseased cell. The "guide RNA" as described herein may consist of two RNAs, namely, crRNA and tracrRNA, or be a single guide RNA (sgRNA) produced by fusion of an essential portion of crRNA and tracrRNA.

Accordingly, in another embodiment, the present invention provides a CRISPR-dCas9/dCpf1 system that suppresses MYD88 expression, designed so as to target an expression regulatory region of MYD88 gene (hereinafter also referred to as the "CRISPR-GNDM system of the present invention").

The "CRISPR-GNDM system" described herein means a system comprising (a) a class 2 CRISPR effector protein (e.g., dCas9 or dCpf1) or a complex of said CRISPR effector protein and a transcription regulator (e.g., transcription activators such as VP64, transcription repressors such as Kruppel associated box (KRAB)), and (b) a guide nucleotide (gN) that is complementary to a sequence of an expression regulatory region of a target gene, which allows recruiting the CRISPR effector protein (and the transcription regulator bound therewith) to the expression regulatory region of the target gene, thereby permitting transcriptional control of the target gene via the CRISPR effector protein per se and/or the transcription regulator.

Since the CRISPR-GNDM system recognizes the object double stranded DNA sequence by a guide nucleotide containing a sequence complementary to the target nucleotide sequence and recruits the CRISPR effector (and the transcription repressor bound therewith), any sequence can be targeted by simply designing an oligonucleic acid capable of specifically hybridizing to the target nucleotide sequence.

The CRISPR effector protein to be used in the present invention is not particularly limited as long as it belongs to the class 2 CRISPR system, and preferred is Cas9 or Cpf1. Examples of Cas9 include, but are not limited to, *Streptococcus pyogenes*-derived Cas9 (SpCas9; PAM sequence NGG (N is A, G, T or C. The same shall apply hereinafter.)), *Streptococcus thermophilus*-derived Cas9 (StCas9; PAM sequence NNAGAAW (W is A or T. The same shall apply hereinafter)), *Neisseria meningitides*-derived Cas9 (MmCas9; PAM sequence NNNNGATT), *Streptococcus aureus*-derived Cas9 (SaCas9; PAM sequence NNGRRT (R is A or G. The same shall apply hereinafter.)), *Campylobacter jejuni*-derived Cas9 (CjCas9; PAM sequence NNNVRYM(C) (Y is T or C. M is A or C. The same shall apply hereinafter.)), and the like. Examples of Cpf1 include, but are not limited to, Lachnospiraceae bacterium-derived Cpf1(LbCpf1; PAM sequence TTTN), *Francisella novicida*-derived Cpf1 (FnCpf1; PAM sequence TTN), *Acidaminococcus* sp.-derived Cpf1 (AsCpf1; PAM sequence TTTN) and the like.

Preferably, Cas9 is SpCas9 or its derivatives that are less limited by PAM (since SpCas9 PAM is defined by substantially 2 nucleotides (i.e., GG), theoretically, SpCas9 can target almost any position of genome). As a dCas9 to be used in the present invention, any of Cas9 wherein the cleavage ability of the both chains of the double stranded DNA is inactivated can be used. For example, in the case of SpCas9, a double mutant of D10A, wherein the 10th Asp residue is converted to an Ala residue and lacking cleavage ability of a chain opposite to the chain forming a complementary chain with a guide RNA, and H840A, wherein the 840th His residue is converted to an Ala residue and lacking cleavage ability of chain complementary to guide RNA. On the other hand, in the case of Cpf1, while preferred is FnCpf1 that is less limited by PAM (since FnCpf1 PAM is defined by substantially 2 nucleotides (i.e., TT), theoretically, FnCpf1 can target almost any position of genome), LbCpf1 and AsCpf1 whose PAMs are defined by substantially 3 nucleotides (i.e., TTT) are also preferable. As a dCpf1 to be used in the present invention, any of Cpf1 wherein the cleavage ability of the both chains of the double stranded DNA is inactivated can be used. For example, in the case of FnCpf1, D917A, E1006A or D1255A, in the case of AsCpf1, D908A, E993A or D1263A, and in the case of LbCpf1, D832A, E925A, D947A or D1180A can be used, respectively.

As described above, while the CRISPR effector protein such as dCas9/dCpf1 recruited to the expression regulatory region of MYD88 gene via the gRNA can suppress MYD88 expression without co-existence of a transcription repressor, by preventing binding of an endogenous transacting factor, a transcription repressor such as Kruppel associated box (KRAB) motif can be further used in combination with the CRISPR effector protein. In such case, the expression of MYD88 gene can be more potently suppressed by recruiting a complex of the CRISPR effector and the transcription repressor to the expression regulatory region.

The term "transcription repressor" described herein means a protein or a domain thereof having an activity that suppresses transcription of a target gene.

The transcription repressor to be used in the present invention is not limited as long as it can suppress the expression of MYD88 gene, for example, includes Kruppel associated box (KRAB), MBD2B, v-ErbA, SID (including a concatemer of SID (SID4X)), MBD2, MBD3, DNMT family (e.g., DNMT1, DNMT3A, DNMT3B), Rb, MeCP2, ROM2, LSD1 and AtHD2A. Preferred is KRAB.

The transcription repressor can be originated from any organism as long as it can suppress the expression of MYD88 gene. For example, transcription repressors originated from vertebrates (e.g., mammals such as human, porcine, bovine, canine and chimpanzee, Aves such as chicken and the like), preferably mammals, more preferably human, can be used.

As mentioned above, in a preferable embodiment, KRAB is used as the transcription repressor. KRAB is a category of transcriptional repression domains present in approximately 400 human zinc finger protein-based transcription factors (KRAB-ZFPs). The KRAB domain typically consists of about 75 amino acid residues, while the minimal repression module is approximately 45 amino acid residues (Proc. Natl. Acad. Sci. U.S.A. 91(10): 4509-13, 1994). Since human genes encoding KRAB-ZFPs include KOX1/ZNF10, KOX8/ZNF708, ZNF43, ZNF184, ZNF91, HPF4, HTF10 and HTF34, the KRAB domain to be used in the present invention can be cloned from these genes.

In one embodiment, a complex of the CRISPR effector protein (dCas9/dCpf1) and the transcription repressor can be provided in the form of a fused protein. In this case, the KRAB domain can be fused with either N-terminus or C-terminus of the CRISPR effector protein. The resulting dCas9/dCpf1-KRAB protein is recruited to an expression regulatory region within the MYD88 gene (e.g. promoter or enhancer region) via interaction with a gN containing a nucleotide sequence complementary to the target expression regulatory region and thereby exerts its transcriptional repressor effect.

In another embodiment, a protein-binding domain such as SH3 domain, PDZ domain, GK domain, GB domain and the like and a binding partner thereof may be fused with the CRISPR effector protein such as dCas9/dCpf1 and the transcription repressor, respectively, and provided as a protein complex via an interaction of the domain and a binding partner thereof. In another embodiment, the CRISPR effector protein and the transcription repressor may be each fused with intein, and they can be linked by ligation after protein synthesis. The CRISPR effector protein and the transcription repressor can also be bound by utilizing an RNA aptamer such as MS2F6, PP7 and the like and an RNA scaffold constructed by a protein binding to said aptamer. Preferably, one or more nuclear localization signals (NLS) are ligated to the N- and/or C-termini of the CRISPR effector protein, in order to facilitate nuclear transition thereof. When the transcription repressor is used in combination with the CRISPR effector protein, NLS can also be ligated to both or either of N- and C-termini of the transcription repressor. In addition, a tag such as hemagglutinin (HA), fluorescent protein (e.g., GFP) can be bound to the CRISPR effector protein and/or the transcription repressor.

In one preferable embodiment, multiple transcription repressors are recruited to the CRISPR effector protein via the Suntag system (Tanenbaum et al, *Cell* 159, 635-646, 2014). SunTag is a tandem repeat of five copies of the 19 amino-acid GCN4 peptide separated by amino acid linkers of 5, 22, or 43 amino acid residues. The 19-aa GCN4 peptide sequence is recognized by a single-chain variable fragment (scFv) of an anti-GCN4 antibody, to which transcription repressor factor is linked as a fusion molecule. The resulting scFv-transcription repressor molecule is recruited to the 19-aa GCN4 portion of the dCas9/dCpf1-SunTag fusion protein, thereby enabling recruitment of multiple copies of the transcription repressors to dCas9/dCpf1. The resulting dCas9-SunTag-scFv-transcription repressors complex is recruited to the target expression regulatory region within the MYD88 gene (e.g. promoter or enhance region) via a gN specific thereto and thereby exerts its transcriptional repressor effect.

The second element of the CRISPR-GNDM system of the present invention is a gN that contains a nucleotide sequence (hereinafter also referred to as "targeting sequence") complementary to the nucleotide sequence adjacent to PAM of the target strand in the expression regulatory region of MYD88 gene. When the CRISPR effector protein is dCas9, the gN may be provided as a chimeric RNA of truncated crRNA and tracrRNA (i.e., single guide RNA (sgRNA)), or combination of separate crRNA and tracrRNA. The gN may be provided in a form of RNA, DNA or DNA/RNA chimera. Thus, hereinafter, as long as technically possible, the terms "sgRNA", "crRNA" and "tracrRNA" are used to also include the corresponding DNA and DNA/RNA chimera in the context of the present invention. The crRNA contains the targeting sequence. The targeting sequence is not limited as long as it can specifically hybridize with the target strand at an expression regulatory region of MYD88 gene and recruit the CRISPR effector protein (and a transcription repressor bound therewith) to the expression regulatory region. For example, when SpdCas9 is used as the CRISPR effector protein, the targeting sequences listed in Table 1 are exemplified. In Table 1, while targeting sequences consisting of 20 nucleotides are described, the length of targeting sequence can be arbitrarily chosen in the range of 18-25 nucleotides. When SpdCas9 is used as the CRISPR effector protein, the gN to be used in the present invention preferably contains the nucleotide sequences represented by any one of SEQ ID NOs: 5 to 35 (Table 1) as a targeting sequence.

A crRNA containing a targeting sequence other than those listed in Table 2 can be designed and produced based on the nucleotide sequence information of MYD88 gene. When SadCas9 or LddCpf1/AsdCpf1 that recognizes a different PAM is used as the CRISPR effector protein, targeting sequences can be designed and produced in the same manner. Examples of targeting sequences for LddCpf1/AsdCpf1 include, but are not limited to, those listed in Table 2. In Tables 1 and 2, the sequences are indicated as DNA sequences. When an RNA is used as the gN, "T" should be read "U" in each sequence.

TABLE 1

Forty targeting sequences used to screen the region surrounding the MYD88 gene

| SEQ ID NO | Position | strand | Sequence | PAM | Specificity Score | Efficiency Score |
|---|---|---|---|---|---|---|
| 1 | 38129083 | + | GGCGATGTTTGGAAACTCGGGGG | | 86.10 | 64.46 |
| 2 | 38131067 | − | TGTCACCTTCACCTAGACTGTGG | | 70.63 | 67.72 |
| 3 | 38132970 | + | CTTATAACACTGTGCCCTAGAGG | | 77.97 | 63.42 |
| 4 | 38135025 | + | GATAGGAGAAAACCGCCCTGTGG | | 81.70 | 75.53 |
| 5 | 38135828 | + | CTTTACGGGTGTCTGCAAAGAGG | | 73.60 | 71.06 |
| 6 | 38136643 | + | ATTCACGTCCTTGAGAACCGCGG | | 88.41 | 79.53 |
| 7 | 38136875 | + | GCCTCACCTTGAAGCCGCCGCGG | | 83.90 | 59.82 |
| 8 | 38137004 | + | AATCGGCCGGACCCCTCAGGTGG | | 86.60 | 59.38 |
| 9 | 38137232 | + | ACCACAAGGAGAGTCGGCCTGGG | | 85.04 | 56.67 |
| 10 | 38137263 | − | CCTATAGAGGGCTTGGTAGGCGG | | 71.24 | 60.55 |
| 11 | 38137390 | + | CCCCGCCCAGAAATGCAGACCGG | | 66.33 | 58.54 |
| 12 | 38137500 | + | CAGGACCGCTTACTGCTTGGGGG | | 76.05 | 62.11 |
| 13 | 38137629 | + | GCCCGAGTCCTGCTCCGACGTGG | | 87.76 | 64.81 |
| 14 | 38137852 | + | AGAGAGGTACCATGTATCCGGGG | | 83.61 | 69.00 |
| 15 | 38137987 | − | CCCTGCTATTGGGAGTCAAGGGG | | 69.36 | 61.66 |
| 16 | 38138176 | + | CGTTTCCCACTCCCACCTCGGGG | | 60.46 | 67.48 |
| 17 | 38138323 | + | GAACCCCTCAGATTCCTCCGTGG | | 80.22 | 73.19 |
| 18 | 38138442 | + | CATCACCAGACCCTCGAGGGCGG | | 72.42 | 70.66 |
| 19 | 38138556 | − | TGGAGCCCCGAGCAAAAGTGCGG | | 76.95 | 68.72 |
| 20 | 38138614 | + | TCGGAAAGCGAAAGCCGGCGGGG | | 89.95 | 62.78 |
| 21 | 38138785 | + | CTGCTCTCAACATGCGAGTGCGG | | 90.54 | 63.32 |
| 22 | 38138949 | − | GTCGGCCTACAGAGGCGCCAGGG | | 84.18 | 60.12 |
| 23 | 38139082 | + | GTGAGGAGGCTGACTTTCCGCGG | | 72.92 | 60.98 |

TABLE 1-continued

Forty targeting sequences used to screen the region surrounding the MYD88 gene

| SEQ ID NO | Position | strand | Sequence | PAM | Specificity Score | Efficiency Score |
|---|---|---|---|---|---|---|
| 24 | 38139228 | + | GACTGGAGAAAGGTCCGGATAGG | | 86.50 | 61.94 |
| 25 | 38139356 | + | ACAGGTGGGCGATTGACAGTGG | | 77.49 | 64.10 |
| 26 | 38139505 | + | AATCACTGCACCATAACCAGTGG | | 69.65 | 70.35 |
| 27 | 38139610 | + | ATTCTTAGGATCCCTAGGAAGGG | | 63.64 | 61.99 |
| 28 | 38139723 | − | TGGTGCCACGCGAAGCTCAACGG | | 90.85 | 64.30 |
| 29 | 38139998 | − | AGTATTGGACCCTTACCCAGGGG | | 80.52 | 80.20 |
| 30 | 38140584 | + | AGGTTGGCTAGAAGGCCACGGGG | | 79.69 | 76.44 |
| 31 | 38141036 | + | TGCCAGGGGTACTTAGATGGGGG | | 78.08 | 65.14 |
| 32 | 38141462 | − | CACAGCCACTGGTTCCATGCAGG | | 70.12 | 60.04 |
| 33 | 38141894 | − | AGGAAATAAGGCTCAAGGTGGGG | | 63.78 | 65.67 |
| 34 | 38142043 | − | GGAGCTGAGAGCATGACCACAGG | | 64.23 | 61.93 |
| 35 | 38143160 | + | CACAGGTTCAGTCCTAAGCAGGG | | 67.79 | 66.20 |
| 36 | 38144099 | + | ACTACGATTCTGTGTGACGATGG | | 92.30 | 60.23 |
| 37 | 38145033 | − | TTGGGGTATATACTCCCAAGTGG | | 76.52 | 61.44 |
| 38 | 38146018 | + | TACTAGCCAAACGACCAGAAAGG | | 81.64 | 60.13 |
| 39 | 38147089 | + | ACCCCAAGAAATCCACACCAAGG | | 61.42 | 70.70 |
| 40 | 38147832 | + | GAGTCAAGGCACTTAAAGCAAGG | | 64.64 | 63.66 |

TABLE 2

Examples of targeting sequences for LddCpf1/AsdCpf1

| SEQ ID NO | Position | Strand | Sequence | PAM | Specificity Score | Efficiency Score |
|---|---|---|---|---|---|---|
| 41 | 38137165 | − | GAGGGTCGCTCGCGTCTGTTCGCA | TTTG | 99.90 | NA |
| 42 | 38137166 | − | GGAGGGTCGCTCGCGTCTGTTCGC | TTTT | 99.79 | NA |
| 43 | 38137363 | − | TGGGCGGGGATTCGTAAAGATACA | TTTC | 99.25 | NA |
| 44 | 38137387 | + | CGAATCCCCGCCCAGAAATGCAGA | ITTA | 98.71 | NA |
| 45 | 38137419 | − | GGGGTCAGGTCTCGGGTTTGGCTA | TTTG | 98.13 | NA |
| 46 | 38137432 | + | GTAGCCAAACCCGAGACCTGACCC | TTTT | 98.19 | NA |
| 47 | 38137433 | + | TAGCCAAACCCGAGACCTGACCCC | TTTG | 98.62 | NA |
| 48 | 38137577 | − | GGTCCCCCAGCTCGGGTACTGGGA | TTTA | 98.70 | NA |
| 49 | 38137692 | + | GGCTTCCGGGCTGGCCGGGAGAAC | TTTG | 98.89 | NA |
| 50 | 38137723 | + | ACAGACATGCGGGGTGTGACAAGC | TTTT | 98.05 | NA |
| 51 | 38138392 | + | CTACAACCCCGAAGGAGGGTCGT | TTTC | 98.82 | NA |
| 52 | 38138452 | − | GAGATCTGGAGAGGTCCACGGCAC | TTTT | 99.14 | NA |
| 53 | 38138581 | − | CGAGAAGCGCCGCCCTGCCCTACA | TTTC | 99.28 | NA |
| 54 | 38138587 | − | GCTTTCCGAGAAGCGCCGCCCTGC | TTTC | 99.36 | NA |
| 55 | 38138620 | − | TCCTGCGGCACCCGCCCCGCCCCG | TTTC | 98.45 | NA |

TABLE 2-continued

Examples of targeting sequences for LddCpf1/AsdCpf1

| SEQ ID NO | Position | Strand | Sequence | PAM | Specificity Score | Efficiency Score |
|---|---|---|---|---|---|---|
| 56 | 38139102 | + | CGCGGCCTCAGCATCCTGTCTCCC | TTTC | 98.73 | NA |
| 57 | 38139144 | + | CTGCCTCGGGGGCCCGAAGAAGCC | TTTC | 99.48 | NA |
| 58 | 38139857 | − | GGCAATCCTCCTCTGTGGGAAGA | TTTT | 97.95 | NA |
| 59 | 38139942 | + | CAGGTGGCCGCTGTAGACAGCAGT | TTTA | 98.15 | NA |
| 60 | 38141891 | + | GCCCAGCCCAAGGAGACCCCACCT | TTTG | 98.64 | NA |

Figure 1B:
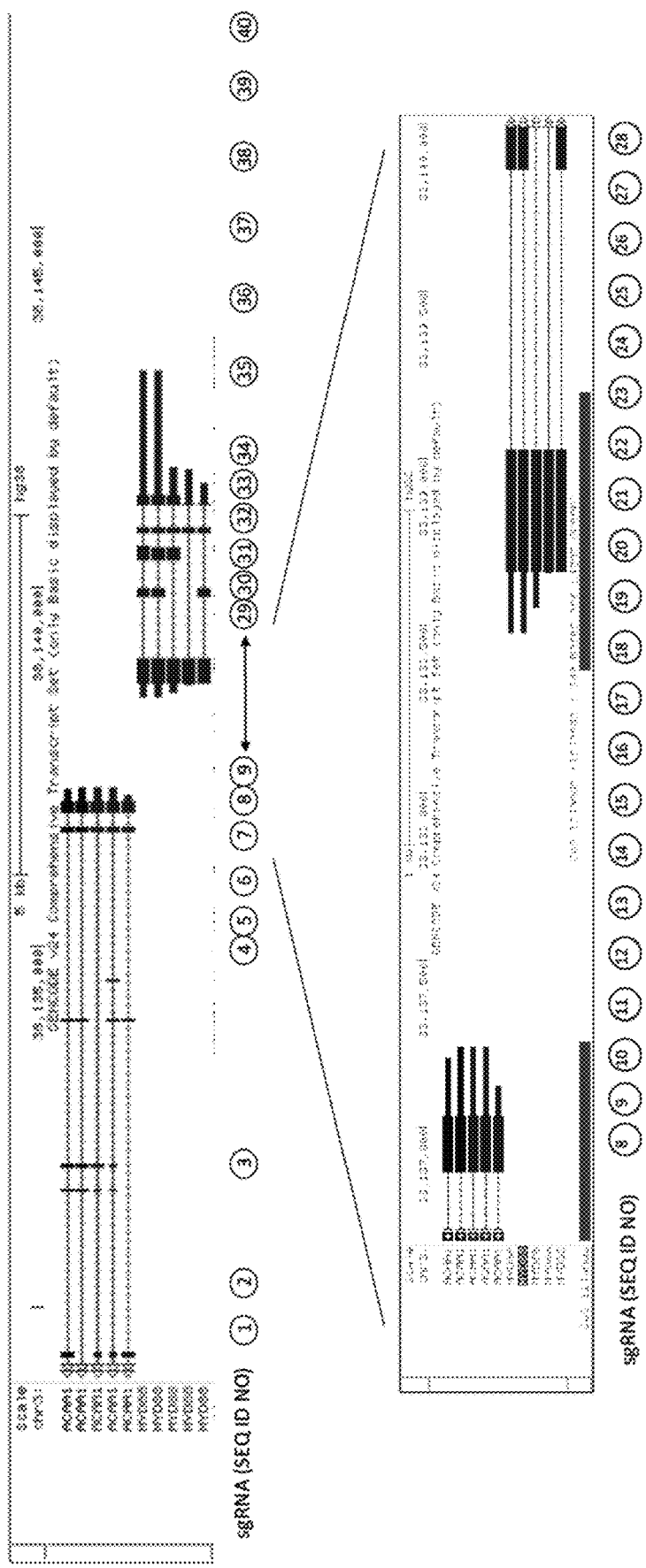
FIG. 1B shows the region at positions 38,129,000-38,148,000 of human chromosome 3 (GRCh38/h38 human genome assembly; CM000665) that includes the whole MYD88 gene and some of the ACAA1 gene. Forty guide RNA sequences were designed to target the region in and around the ACAA1 and MYD88 gene in order to determine the most effective and selective therapeutic sequence within this region.

However, it can be any gN targeting a part of the defined region (5.9 kb) having the nucleotide sequence at positions 1,405-7,352 of SEQ ID NO: 65, which corresponds to positions 38,137,215 to 38,143,160 of human chromosome 3 (CM000665). This region was identified in the screening of forty sgRNAs surrounding the MYD88 gene that enables efficient suppression of the MYD88 gene while not affecting the ACAA1 gene that is only ~1.2 kb apart from the MYD88 gene (FIG. 1B).

As shown in the following Examples (FIG. 2), when the expression regulatory region of MYD88 gene is a region including DNA sequence targeted by the targeting sequences shown by SEQ ID NO: 5 to SEQ ID NO: 35, a high suppressive effect on the MYD88 gene expression was shown. Therefore, not only a gN containing any of the sequences described in Tables 1 and 2 but also any gN containing a targeting sequence at least a part of which targets a sequence within such expression regulatory region is expected to show a high suppressive effect. Specifically, as such expression regulatory region of MYD88 gene to be targeted, a region (about 7.4 kb) having the nucleotide sequence shown by SEQ ID NO 65, can be mentioned, a region (about 5.9 kb) at positions 1,405-7,352 of SEQ ID NO: 65 is more preferable. Such region (about 5.9 kb) was identified in the screening of forty sgRNAs surrounding the MYD88 gene that enables efficient suppression of the MYD88 gene while not affecting the ACAA1 gene that is only ~1.2 kb apart from the MYD88 gene (FIG. 1B).

The targeting sequences thus designed can be evaluated for its off-target activities. For initial screening of predicted off-target activities, there are a number of bioinformatics tools known and publicly available that can be used to predict the most likely off-target sites; and since binding to target sites in the CRISPR-GNDM system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called Benchling (benchling.com) and COSMID (CRISPR Off-target Sites with Mismatches, Insertions and Deletions) (available on the web at crispr.bme.gatech.edu) compiles such similarities.

The crRNA containing a sequence complementary to the target strand of the target nucleotide sequence can be ligated to a tracrRNA necessary for recruiting dCas9 protein to give an sgRNA. When the gRNA is brought into contact with the subject genome, the crRNA in the gRNA is hybridized to the target strand of the expression regulatory region of interest and tacrRNA ligated to 3'-end of the crRNA recruits dCas9 protein to recognize PAM. Alternatively, the crRNA and tracrRNA can be provided separately, and assembled in a host cells of interest to form a guide RNA (gRNA). Since the dCas9 protein is inactivated, it does not cleave the genome. Instead, due to the presence of the dCas9 protein in the expression regulatory region of MYD88 gene and/or the action of the transcription repressor bound to the dCas9 protein on the expression regulatory region, the expression of MYD88 gene is suppressed. On the other hand, when the CRISPR effector protein is Cpf1, the gRNA can only consist of crRNA, wherein the crRNA contains a targeting sequence complementary to the target strand of the target nucleotide sequence and 5'-handle sequence ligated to 5'-end of the targeting sequence, which is necessary for recruiting dCpf1 protein to the target expression regulatory region.

In one embodiment, two or more gNs that have different targeting sequences complementary to different expression regulatory regions of MYD88 gene can be used. In this case, more potent suppressing effect on the expression of MYD88 gene can be expected.

<<Nucleic Acids Encoding CRISPR-GNDM System>>

The CRISPR-GNDM system of the present invention comprising (a) a CRISPR effector protein such as dCas9/dCpf1 or a complex of the CRISPR effector protein and a transcription repressor, and (b) a gN containing a targeting sequence complementary to the target strand of an expression regulatory region within MYD88 gene can be introduced into a diseased cell in an organism to be treated in the form of DNAs encoding (a) and (b) above. A DNA encoding Cas9 or Cpf1 can be cloned by, for example, synthesizing an oligo DNA primer covering CDS based on the cDNA sequence information thereof, and amplifying by the RT-PCR method using, as a template, the total RNA or mRNA fraction prepared from Cas9- or Cpf1-producing cells. A DNA encoding dCas9/dCpf1 can be obtained by introducing a mutation to convert an amino acid residue of the part important for the DNA cleavage activity (e.g., 10th Asp residue and 840th His residue for SpCas9, 908th Asp, 993rd Glu or 1263rd Asp residue for AsCpf1, though not limited thereto) to other amino acid, into the cloned DNA encoding Cas9, by a site-directed mutagenesis method known per se.

Alternatively, a DNA encoding dCas9/dCpf1 can be obtained by chemically synthesizing the DNA chain, or by connecting synthesized partly overlapping oligo DNA short chains by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database (www.kazusa.or.jp/codon/index.html) disclosed in the home page of Kazusa DNA Research Institute can be used, or documents showing the codon usage frequency in each host may be referred to. By reference to the obtained data and the DNA sequence to be introduced, codons showing low usage frequency in the host from among those used for the DNA sequence may be converted to a codon coding the same amino acid and showing high usage frequency.

A DNA encoding a transcription repressor can also be cloned from a cell that produces the same. For example, a DNA encoding KRAB domain derived from human KOX-1 can be cloned by designing suitable primers for the upstream and downstream of coding region of said KRAB domain based on the cDNA sequence of KOX-1 (accession No. NM_015394.4) registered in the NCBI database, and cloning from human-derived mRNA fraction by the RT-PCR method. Alternatively, A DNA encoding a transcription repressor can be constructed as a DNA having codon usage suitable for expression in an organism to be introduced using chemical synthesis (optionally in combination with PCR method or Gibson Assembly method).

The cloned DNA encoding a transcription repressor can be directly, or after digestion with a restriction enzyme, or after addition of an adequate linker and/or an NLS, ligated to a DNA encoding a CRISPR effector protein to give a DNA encoding a fused protein. Alternatively, a DNA encoding a CRISPR effector protein, and a DNA encoding a transcription repressor may be each fused with a DNA encoding a binding domain or a binding partner thereof, or both DNAs may be fused with a DNA encoding an intein, whereby the CRISPR effector protein and the transcription repressor are translated in a host cell to form a complex. In these cases, a linker and/or an NLS can be linked to a suitable position of either or both of the DNAs when desired. When SunTag is used for recruiting multiple transcription repressors, a DNA encoding a CRISPR effector protein and a DNA encoding SunTag that contains tandem repeats of GCN4 peptide intermediated by a linker peptide are directly or indirectly fused or post-translationally combined using suitable binding partners in the same manner as described above. Also, a DNA encoding a fragment (e.g., scFv) of an anti-GCN4 peptide antibody and a DNA encoding a transcription repressor are fused in the same manner. When the DNA encoding dCas9/dCpff1-Suntag and the DNA encoding anti-GCN4 antibody-transcription repressor are co-expressed within a host cell, a multiple transcription repressors-CRISPR effector protein complex can be formed in the cell.

A DNA encoding the gRNA of the present invention discussed in detail above can be chemically synthesized using a DNA/RNA synthesizer based on its sequence information. For example, a DNA encoding an sgRNA for dCas9 has a deoxyribonucleotide sequence encoding a crRNA containing a targeting sequence complementary to an expression regulatory region of MYD88 gene and at least a part of the "repeat" region (e.g., GUUUUAGAGCUA; SEQ ID NO:61) of the native SperRNA, and a deoxyribonucleotide sequence encoding tracrRNA having at least a part of the "anti-repeat" region complementary to the repeat region of the crRNA (e.g., UAGCAAGUUAAAAU; SEQ ID NO:62) and the subsequent stem-loop 1, linker, stem-loop 2 and stem-loop 3 regions (AAGGCUAGUCCGUUAU-CAACUUGAAAAAGUGGCACCGAGUCGGUGCUU; SEQ ID NO:63) of the native SptracrRNA, optionally linked via a tetraloop (e.g., GAAA). On the other hand, a DNA encoding a gRNA for dCpf1 has a deoxyribonucleotide sequence encoding a crRNA alone, which contains a targeting sequence complementary to an expression regulatory region of MYD88 gene and the preceding 5'-handle (e.g., AAUUUCUACUCUUGUAGAU; SEQ ID NO:64). When a protein other than spCas9 and Cpf1 is used as a CRISPR effector protein, a tracrRNA for the protein to be used can be designed appropriately based on a known sequence and the like.

The DNA encoding the CRISPR effector protein (optionally ligated with the DNA encoding the transcription repressor) can be subcloned into an expression vector such that said DNAs are located under the control of a promoter that is functional in a host cell of interest.

As the expression vector, plasmids for expression in animal cells (e.g., pA1-11, pXT1, pRc/CMV, pRc/RSV, pcDNAI/Neo); vectors derived from animal virus such as retrovirus, vaccinia virus, adenovirus, adeno-associated virus, etc, and the like can be used. When a viral vector is used as the expression vector, a vector derived from a serotype suitable for infecting a diseased organ of interest can preferably be used. For example, in the case of adeno-associated viral (AAV) vector, when the disease to be treated is NASH, AAV8 or AAV9-based vectors more likely to infect liver (e.g., scAAV2/8-LP1-hFIXco) can be preferred.

As the promoter, any promoter appropriate for the host cell can be used. For example, when the host is a mammalian cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

As the expression vector, besides those mentioned above, one containing enhancer, splicing signal, polyadenylation signal, a selectable marker such as drug resistance gene and the like, replication origins for mammalian cell and E. coli and the like be on demand can be used.

The DNA encoding the gRNA can also be subcloned into the expression vector mentioned above, but pol III-type promoters (e.g., SNR6, SNR52, SCR1, RPR1, U6 and H1 promoters) and terminators (e.g., $T_6$ sequence) can preferably be used. When a pol III promoter is used, a nucleotide sequence containing 4 or more T residue repeats should be avoided to use as a targeting sequence.

The DNA encoding the CRISPR effector protein or the complex of the CRISPR effector protein and the transcription repressor and the DNA encoding the gRNA can be inserted into separate vectors, respectively, or into a single vector. Also, when the complex of the CRISPR effector protein and the transcription repressor is formed via a pair of binding partners as mentioned above, the DNA encoding the CRISPR effector protein (including SunTag-fused dCas9/dCpf1) and the DNA encoding the transcription repressor (including anti-GCN4 scFv-fused transcription repressor) can be inserted into separate vectors, respectively, or into a single vector.

The gN of the CRISPR-GNDM system of the present invention can also be chemically synthesized using a DNA/RNA synthesizer, and introduced into a host cell of interest, as it is (i.e., without being inserted into a vector).

Alternatively, an RNA can be used instead of the DNA to deliver CRISPR effector molecule. In one embodiment, the CRISPR-GNDM system of the present invention comprising (a) a CRISPR effector protein such as dCas9/dCpf1 or a complex of the CRISPR effector protein and a transcription repressor, and (b) a gN containing a targeting sequence complementary to the target strand of an expression regulatory region within MYD88 gene can be introduce into a diseased cell in an organism to be treated in the form of RNAs encoding (a) and (b) above. For example, an RNA encoding the effector molecules above can be generated via in vitro transcription, and the generated mRNA can be purified for in vivo delivery. Briefly, a DNA fragment containing the CDS region of the effector molecules can be cloned down-stream of an artificial promoter from bacteriophage driving in vitro transcription (e.g. T7 T3 or SP6 promoter). The RNA can be transcribed from the promoter by adding components required for in vitro transcription such as T7 polymerase, NTPs, and IVT buffers. If need be, the RNA can be modified to reduce immune stimulation, enhance translation and nuclease stability (e.g. 5mCAP (m7G(5')ppp(5')G capping, ARCA; anti-Reverse Cap Analogs (3' O-Me-M7G(5')ppp(5')G), 5-methylcytidine and pseudouridine modifications, 3' poly A tail).

Alternatively, a complex of an effector protein and a gN, hereafter termed nucleoprotein (NP) (e.g., deoxyribonucleoprotein (DNP), ribonucleoprotein (RNP)), can be used to deliver CRISPR effector molecule and gN. Briefly, in vitro generated CRISPR effector protein and in vitro transcribed or chemically synthesized gN are mixed at appropriate ratios, and then encapsulated into Lipid nanoparticles (LNPs). The encapsulated LNPs can be delivered into a patient and the NP complex can be delivered directly into target cells or organs.

For example, a CRISPR effector protein can be expressed in bacteria and can be purified via affinity column. Bacteria codon-optimized cDNA sequence of the CRISPR effector protein can be cloned into bacteria expression plasmids such as pE-SUMO vector from LifeSensors. The cDNA fragment can be tagged with a small peptide sequence such as HA, 6×His, Myc, or FLAG peptides, either on N- or C-terminus. The plasmids can be introduced into protein-expressing bacterial strains such as *E. coli* B834 (DE3). After induction, the protein can be purified using affinity column binding to the small peptide tag sequences, such as Ni-NTA column or anti-FLAG affinity column. The attached tag peptide can be removed by TEV protease treatment. The protein can be further purified by chromatography on a HiLoad Superdex 200 16/60 column (GE Health-care).

Alternatively, the CRISPR effector protein can be expressed in mammalian cell lines such as CHO, COS, HEK293, and Hela cell. For example, human codon-optimized cDNA sequence of the CRISPR protein can be cloned into mammalian expression plasmids (e.g., pA1-11, pXT1, pRc/CMV, pRc/RSV, pcDNAI/Neo, pSRa); vectors derived from animal virus such as retrovirus, vaccinia virus, adenovirus, adeno-associated virus, etc, and the like can be used. The cDNA fragments can be tagged with a small peptide sequence such as HA, 6×His, Myc, or FLAG peptide, either on N- or C-terminus. The plasmids can be introduced into the protein-expressing mammalian cell lines. 2-3 days after the transfection, the transfected cells can be harvested and the expressed CRISPR protein can be purified using affinity column binding to the small peptide tag sequences said above.

The purified CRISPR protein can be mixed with gN synthesized at different ratio (e.g. 10:1, 5:1, 2:1 1:1, 1:2, 1:5, 1:10) and can be encapsulated into LNPs under optimum conditions.

<<Introduction of CRISPR-GNDM System>>

A method of introducing the CRISPR-GNDM system of the present invention is not limited as long as the CRISPR-GNDM system can be efficiently and/or selectively delivered to a diseased site of interest. In a preferable embodiment, access for the target organ can be carried out by AAV injection. An expression vector carrying the DNA encoding the CRISPR-GNDM system (i.e., dCas9/dCpf1 or a complex of dCas9/dCpf1 and transcription repressor, and gN that targets an expression regulatory region of MYD88 gene) is injected intravenously (in the case of a viral vector such as AAV, the vector is administered in an amount of $1\text{-}10\times10^{12}$ viral genome(vg)/kg). For diseases other than NASH, local injection methods established for various target organs can also be used.

The serotype of AAV employed to deliver medicine depends on the tropism of the serotype to a target organ or cell-type. The most preferred serotype for liver, where NASH occurs, can be AAV serotypes 8 and 9. For diseases involving other organs or cell-types, a most preferred serotype from AAV1, AAV2, AAV3, AAV4, AAV5, AAV6, and AAV7 can be chosen.

In other embodiment, (1) a non-viral expression vector carrying the DNA encoding the CRISPR effector protein or the complex of the CRISPR effector protein and the transcription repressor, and (2) (a) a non-viral expression vector carrying the DNA encoding the gRNA or (b) the gN per se. can be introduced intravenously or locally into the lesion of interest using biologically compatible nanoparticles.

In other embodiment, mRNA encoding the CRISPR effector protein or the complex of the CRISPR effector protein and the transcription repressor, and in vitro-transcribed or chemically synthesized gN can be introduced into lesion of interest using biologically compatible nanoparticles.

In other embodiment, the CRISPR effector protein or the complex of the CRISPR effector protein and the transcription repressor, and in vitro-transcribed or chemically synthesized gN can be introduced into lesion of interest using biologically compatible nanoparticles.

The biologically compatible nanoparticles in which the DNA encoding the CRISPR-GNDM system include, but are not limited to, polylactic acid (PLA), polyglycolic acid (PGA), lactic acid-glycolic acid copolymer (PLGA), poly-ε-caprolactone, poly-β-hydroxybutyric acid and the like. Preferred is PLA, PGA, PLGA and the like, more preferably PLGA. A preparation containing the DNA and the biologically compatible nanoparticles, for example, can be formulated according to the method described in JP 2011-111429 A. To be specific, this method comprises a step of providing the biologically compatible nanoparticles as a solution containing the same, and a step of distilling a good solvent away from the solution to give a suspension of the nanoparticles. The biologically compatible nanoparticle has a molecular weight preferably in the range of 5,000-200,000, more preferably in the range of 15,000-25,000. When the biologically compatible nanoparticle is PLGA, the ratio of lactic acid to glycolic acid may be 1:99 to 99:1. The particle size of the biologically compatible nanoparticle is not limited as long as the biologically compatible nanoparticle can deliver the DNA contained therein to a diseased site of interest and introduce the same into the target cells (thereby suppressing the expression of MYD88 gene in the target cells). For example, the particle size is preferably 500 nm or less, more preferably 300 nm or less, as the mean diameter in the final preparation. The content of the DNA in the preparation is typically 0.5 or more % by weight and 30 or less % by weight. Since a plasma membrane in a living body is negatively charged, adhesiveness of the nanoparticle against the plasma membrane can be increased to improve internalization efficiency of the nanoparticle, by subjecting the surface of the nanoparticle to a ξ potential using a cationic polymer.

The preparation of the DNA encoding the CRISPR-GNDM system-capsulated nanoparticles can also be introduced into the target diseased site using intravenous injection or local needle injection as mentioned above.

The suppression efficiency of MYD88 gene expression of the CRIPR-GNDM system of the present invention can be evaluated, for example, by introducing the DNA or RNA or NP encoding the CRIPR-GNDM system into a human cell in vitro, culturing the human cell for a certain period and determine an amount of MYD88 mRNA or MYD88 protein in the human cell by a method known per se.

2. Pharmaceutical of the Present Invention

The present invention also provides a pharmaceutical comprising the nucleic acid mentioned above (including an expression vector containing the same) (hereinafter referred to as the "pharmaceutical of the present invention"). The pharmaceutical of the present invention can be used for the treatment of diseases associated with elevated activity and/or expression of MYD88. The diseases associated with elevated activity and/or expression of MYD88 are as described above.

The active ingredient of the pharmaceutical of the present invention, the CRISPR-GNDM system alone, or in combination with suitable additives conventionally used in the art, can be formulated into the pharmaceutical. The CRISPR-GNDM system is preferably used in the form of nucleic acid, more preferably in the form of expression vector carrying the DNA encoding the CRISPR-GDNM system. Said expression vector may be a viral vector or a non-viral vector. In the case of viral vector, said vector can be prepared as a viral particle encapsulating the DNA encoding the CRISPR-GNDM system therein. In the case of non-viral vector, said vector can be provided in the form that is encapsulated in a biologically compatible nanoparticle.

The pharmaceutical of the present invention can be prepared as a pharmaceutical composition by admixing the active ingredient (i.e., the CRISPR-GNDM system) with known pharmaceutically acceptable carrier(s) including excipient, diluent, extender, binder, lubricant, fluidizer, disintegrant, surfactant and the like) or conventional additive (s). Examples of excipient include phosphate buffered saline (e.g., 0.01 M phosphate, 0.138 M NaCl, 0.0027 M KCl, pH 7.4), a solution containing an inorganic acid salt such as hydrochloride, hydrobromate, phosphate, sulfate or the like, saline, glycol or ethanol solution, a solution of organic acid salt such as acetate, propionate, malonate, benzoate or the like, and the like. Adjuvant(s) such as moistening agent, emulsifier and the like, and pH adjuster can also be used. Furthermore, formulation auxiliaries such as suspending agent, preservative, stabilizer, dispersant and the like may also be used. The pharmaceutical composition may be formulated in the form of dried product for re-dissolving or re-suspending with a suitable sterilized fluid immediately before use. The pharmaceutical composition can be systemically or topically administered according to dosage form, lesion area to be treated and the like. Preferably, it is topically administered. When the pharmaceutical composition is used as an injectable solution, a pharmaceutically acceptable buffer, solubilizing agent, tonicity agent or the like can be added.

The dose of the pharmaceutical of the present invention is not limited as long as it is a therapeutically effective amount. For example, when the pharmaceutical of the present invention contains the DNA encoding the CRISPR-GNDM system in the form of a viral vector, it can be administered in an amount of $10^{11}$ to $10^{13}$ vg/kg, preferably $10^{12}$ to $10^{13}$ vg/kg (as the DNA amount). The dose can vary according to kind of nucleic acid or vector, administration route, and body weight or seriousness of patient, and the like.

Since the pharmaceutical of the present invention can suppress the expression of mutant and wild-type MYD88 gene, it can restore the effectiveness of a known drug for a disease that has acquired resistance to said drug due to gain-of-function mutation of MYD88 (e.g., L265P), including hematological malignancies such as Waldenstrom macroglobulinemia, lymphomas and leukemias. Accordingly, pharmaceutical of the present invention can be used in combination with such known drug. Examples of such drug include, but are not limited to, an antibody medicine against CD20 (e.g., rituximab, ofatumumab) in the case of hematological malignancies with mutation in MYD88 gene.

When the pharmaceutical of the present invention is used in combination with other drug, both can be mixed by a method known per se to give a fixed-dose drug, or the pharmaceutical of the present invention and other drug can be separately formulated and simultaneously or intermittently administered to the same subject. Said other drug can be administered in an amount typically used for its sole administration.

EXAMPLES

The invention will be more fully understood by reference to the following examples, which provide illustrative non-limiting embodiments of the invention.

The examples describe the use of the CRISPR-Guide Nucleotide Directed Modification (GNDM) system to suppress gene expression collectively termed "genomic modifications" herein, in the defined MYD88 gene regulatory region that leads to the selective suppression of MYD88 gene expression. The goal of the modifications is to reduce the impact of wild-type and oncogenic MYD88 products that sustain chronic inflammation triggered through TLRs and IL-1R, and the aberrant tumor cell propagation in hematological malignancies, respectively. The example also describes the definition of a specific genomic region that confers selective suppression of the MYD88 gene without minimally affecting the expression of the adjacent gene ACAA1. Introduction of the defined therapeutic modifications represents a novel therapeutic strategy for the amelioration of tumor cell growth as described and illustrated herein.

Example

Suppression of MYD88 Gene Expression with CRISPR-GNDM System

In this example, we illustrate use of the methods described herein to achieve the suppression of the MYD88 gene through targeting the defined ~6.2 kb region of the MYD88 gene. The methods leverage the property of Cas9-sgRNA molecules, termed RNP, to be recruited to a desired locus of the genome by choosing an appropriate sgRNA sequence. The methods also leverage the nuclease-inactive nature of the SpCas9 protein (D10A and H840A mutant; SpdCas9) to leave the genomic sequence intact, but tether various transcriptional/epigenetic functional domains or motifs to dCas9 to achieve desired modifications of the intended loci targeted by the sgRNA sequence, as described in Gilbert et al., Cell 154, 442-451, 2013, and Gilbert et al., Cell 159, 647-661, 2014.

In this example, we illustrate that the CRISPR-GNDM system can be used to suppress the expression of wild type MYD88. However, the system is expected to suppress the oncogenic MYD88 (L265P) gene as well. Guide RNAs were designed to target the region of the MYD88 gene that confers selective and effective suppression. FIG. 1A shows the human MYD88 locus and a predicted transcript start site (TSS). The TSS of MYD88 gene was identified by querying FANTOM5 human promoterome data base (www.fantom.gsc.riken.jp, Nature 507; 462-470, 2014). FIG. 1B shows the region in Chr3: GRCh38/hg38; 38,129,000-38,148,000 that includes the whole MYD88 gene and some of the ACAA1 gene. Guide RNA sequences were designed to cover the region above in order to determine the effective and selective therapeutic sequences within this region.

Experimental Methods

Selection of sgRNA Sequence

The sequence surrounding the MYD88 gene (~20 kb), including promoter upstream region, introns, exons, 3'UTR and the downstream region, (Chr3: GRCh38/hg38; 38,129,000-38,148,000) were scanned for potential recognition sequences where SpdCas9-sgRNA RNP complex would bind. The region also includes ACAA1 gene that reside ~1.2 kb upstream of the MYD88 gene to evaluate for a potential off-target suppression to the gene. The region was scanned for protospacer adjacent motifs (PAMs) having the sequence NGG. Guide strands corresponding to the PAMs were identified. The guide sequences were selected based on predicted on-target and off-target scores generated by Benchling software (benchling.com), and to be evenly distributed across the selected region.

For initial screening of predicted off-target activities, there are a number of bioinformatics tools known and publicly available that can be used to predict the most likely off-target sites; and since binding to target sites in the CRISPR-Cas9 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called Benchling (benchling.com) and COSMID (CRISPR Off-target Sites with Mismatches, Insertions and Deletions) (available on the web at https://crispr.bme.gatech.edu) compiles such similarities.

The forty sgRNA guide sequences listed in Table 1 were tested for modulation function of the MYD88 gene expression.

The location of the guide RNA target sites surrounding the MYD88 gene is shown in FIG. 1B.

The selected crRNA sequences were fused with the tracer RNA sequence to form single-molecule guide RNA (sgRNA) sequences, and were cloned into pCRISPR-LvSG03 sgRNA expressing vector from Genecopoeia. The sgRNA expression is driven by the U6 promoter, and the vector expresses mCherry-IRES-Puromycin gene under the SV40 promoter to facilitate tracking and selection of the sgRNA expressing cells.

Cloning of Effector Molecule

Catalytically inactive SpCas9 protein (D10A and H840A; SpdCas9) (SEQ ID NO: 66) serves as a main scaffold to tether functional domains/motifs via in a form of direct fusion proteins or via multimer recruiting technologies (e.g. SunTag-scFv, SAM). SpdCas9 is attached with HA-tag peptide (SEQ ID NO: 67) in its N-terminus for tracking and detection purposes, and with two nuclear localization signal (NLS) (SEQ ID NO: 68) in its N- and C-termini to enable efficient localization of the effector molecules to the nucleus. Throughout the examples, dCas9 denotes the HA-NLS-SpdCas9 (D10A and H840A)-NLS molecule (SEQ ID NO: 69).

In one example, dCas9 protein is fused with Kruppel associated box (KRAB) motif, the 75 amino acids transcriptional repression domain, on its N- or C-terminus. The resulting dCas9-KRAB protein is recruited to transcriptionally regulatory regions within the MYD88 gene (e.g. promoter or enhance region) and thereby exerts its transcriptional repressor effect. As a consequence, the expression of MYD88 gene is suppressed.

For the expression of dCas9-KRAB fusion protein, a DNA fragment encoding the dCas9-KRAB fusion protein was cloned into CP-LvC9NU-09 lentivirus expressing vector from Genecopoeia. The Cas9 coding sequence in the original vector was replaced with dCas9-KRAB coding sequence, resulting in the generation of CP-LvdCas9-KRAB-09 plasmid. The vector uses EF1a promoter for the expression of the effector molecules, and SV40 promoter to express eGFP-IRES-Neomycin gene.

Cell Culture and Transfection

HEK293FT cells were seeded 24 hours prior to transfection in 24-well plates at a density of 75,000 cells per well and cultured in DMEM media supplemented with 10% FBS and 2 mM fresh L-glutamine, 1 mM sodium pyruvate and non-essential amino acids. Cells were transfected with 500 ng of dCas9 repressor expressing plasmid and sgRNA expressing plasmid using 1.5 μl of Lipofectamine 2000 (Life technologies), according to manufacturer's instructions.

HEPG2 cells were seeded 24 hours prior to transfection in 24-well plates at a density of 75,000 cells per well and cultured in Eagle's Minimum Essential Medium (EMEM) media supplemented with 10% FBS and 2 mM fresh L-glutamine, 1 mM sodium pyruvate and non-essential amino acids. Cells were transfected with 500 ng of dCas9 repressor expressing plasmid and sgRNA expressing plasmid using 1.0 μl of TrasnfeX (ATCC), according to manufacturer's instructions.

THP1 cells were seeded 24 hours prior to transfection in 24-well plates at a density of 250,000 cells per well and cultured in RPMI media supplemented with 10% FBS and 2 mM fresh L-glutamine, 1 mM sodium pyruvate and non-essential amino acids. Cells were transfected with 500 ng of dCas9 repressor expressing plasmid and sgRNA expressing plasmid using 1.0 μl of GeneXPlus (ATCC), according to manufacturer's instructions.

U937 cells were seeded 24 hours prior to transfection in 24-well plates at a density of 250,000 cells per well and cultured in RPMI media supplemented with 10% FBS and 2 mM fresh L-glutamine, 1 mM sodium pyruvate and non-essential amino acids. Cells were transfected with 500 ng of dCas9 repressor expressing plasmid and sgRNA expressing plasmid using 1.0 μl of GeneXPlus(ATCC), according to manufacturer's instructions.

For gene expression analysis, the transfected cells were harvested at 48-72h after transfection and lysed in RLT buffer (Qiagen) to extract total RNA using RNeasy kit (Qiagen). For protein analysis, the transfected cells were harvested at 96h post-transfection in lysis buffer for RNA isolation and protein analysis as described below.

Gene Expression Analysis

For Taqman analysis, 1.5 µg of total RNA was used to generate cDNA using TaqMan™ High-Capacity RNA-to-cDNA Kit (Applied Biosystems) in 20 µl volume. The generated cDNA was diluted 20 fold and 6.33 µl was used per Taqman reaction. The Taqman primers and probes for the MYD88 gene was obtained from Applied Biosystems. Taqman reaction was run using Taqman gene expression master mix (ThermoFisher) in Roche LightCycler 96 or LightCycler 480 and analyzed using LightCycler 96 analysis software.

Figure 2A:
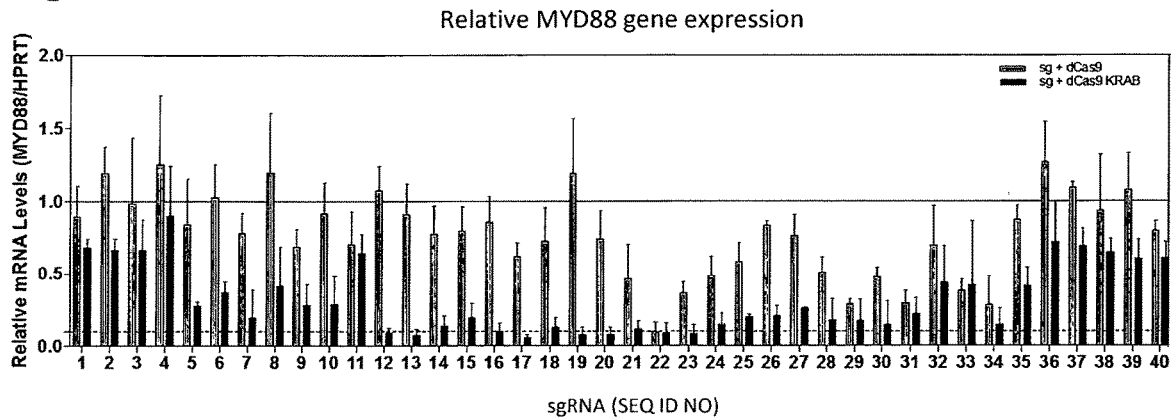
FIG. 2A shows MYD88 gene suppression by dCas9-KRAB fusion protein. HEK293FT cells were co-transfected with 250 ng of CP-LvdCas9-09 plasmid or CP-LvdCas9-KRAB-09 plasmid and 250 ng of the pCRISPR-LvSG03 sgRNA expressing plasmids (SEQ ID NOs:1-40, Table 1) in 24-well plate. The transfected cells were harvested on day 3 and the total RNA was isolated using Qiagen Rneasy kit. The expression level of the MYD88 gene was normalized by the expression of HPRT gene in each sample. The effect of suppression by dCas9-KRAB was shown for each sgRNA relative to no effector (sgRNA only) samples set as 1.0. Experiments were repeated three times and the average and SD were shown.

Taqman Probe Product IDs:
MYD88: Hs01573837_g1 (FAM)
ACAA1: HS01576070_m1 (FAM)
HPRT: Hs99999909_m1 (FAM, VIC)
Taqman QPCR Condition:
Step 1; 95° C. 10 min
Step 2; 95° C. 15 sec
Step 3; 60° C. 30 sec
Repeat Step 2 and 3; 40 times Results FIG. 2A shows the suppression of MYD88 gene expression by SpdCas9 protein alone or SpdCas9-KRAB fusion protein. The sgRNAs of SEQ ID NOs:5 to 35 suppressed MYD88 gene expression by recruiting dCas9 to a regulatory region of MYD88 gene. The suppression effect was enhanced by combining KRAB fusion.

Figure 2B:
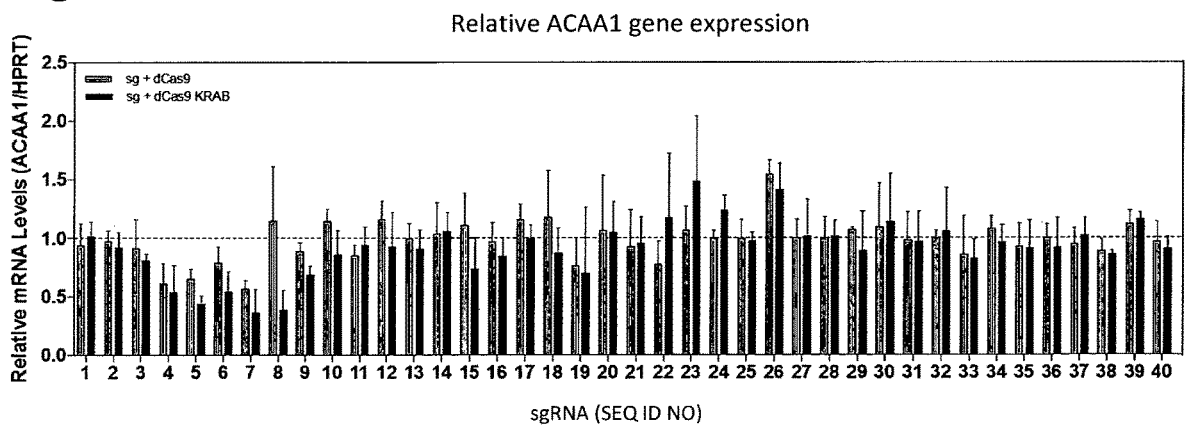
FIG. 2B shows ACAA1 gene suppression in the same experiment. SEQ ID NOs:4 to 8 suppressed the ACAA1 gene expression.
Figure 2C:
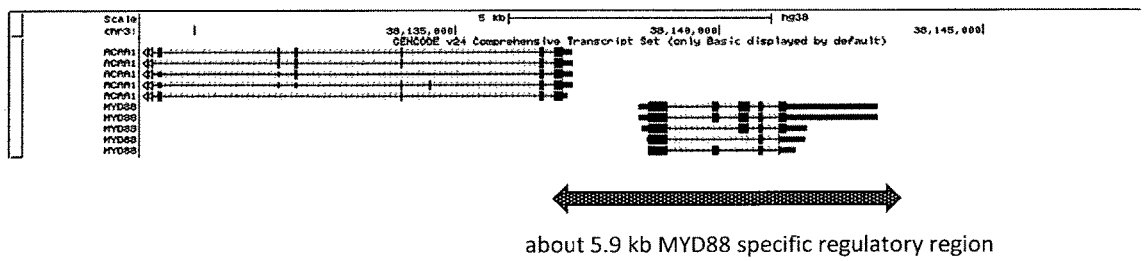
FIG. 2C shows the defined region in and around the MYD88 gene locus that confers the suppression of MYD88 gene while minimally affecting the expression of ACAA1 gene.

FIG. 2B shows the suppression of ACAA1 gene expression in the same experiments. The sgRNAs of SEQ ID NOs: 4 to 8 suppressed ACAA1 gene expression.

From the results above, when the expression regulatory region of MYD88 gene is a region (about 7.4 kb) having the nucleotide sequence shown by SEQ ID NO 65, which includes DNA sequence targeted by the targeting sequences shown by SEQ ID NO: 5 to SEQ ID NO: 35 (Table 1), a high suppressive effect on the MYD88 gene expression was shown (FIG. 2A). Furthermore, when the expression regulatory region of MYD88 gene is a region (about 5.9 kb) having the nucleotide sequence at positions 1,405-7,352 of SEQ ID NO: 65, which includes DNA sequence targeted by the targeting sequences shown by SEQ ID NO: 9 to SEQ ID NO: 35 (Table 1), a high suppressive effect on the MYD88 gene expression was shown (FIG. 2A), and the ACAA1 gene expression was not substantially suppressed (relative mRNA level was within the range of 0.6-1.6) (FIG. 2B). Thus the above region was defined as the MYD88-selective target region.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on U.S. provisional patent application Ser. No. 62/507,340 (filing date: May 17, 2017), the contents of which are incorporated in full herein by this reference.

The invention claimed is:

1. A CRISPR-GNDM system for suppressing MYD88 expression comprising (a) a protein selected from the group consisting of dCas9 or dCpf1, and a fusion protein of dCas9 or dCpf1 and Kruppel associated box (KRAB) or other transcription repressor, and (b) a guide nucleotide (gN) targeting an expression regulatory region of MYD88 gene.

2. The CRISPR-GNDM system according to claim 1, wherein the protein of (a) is selected from the group consisting of dCas9 or dCpf1, and a fusion protein of dCas9 or dCpf1 and Kruppel associated box (KRAB).

3. The CRISPR-GNDM system according to claim 1, wherein the expression regulatory region is a region having the nucleotide sequence set forth in SEQ ID NO: 65.

4. The CRISPR-GNDM system according to claim 1, wherein the expression regulatory region is a region having the nucleotide sequence set forth in positions 1,405-7,352 of SEQ ID NO: 65.

5. The CRISPR-GNDM system according to claim 1, wherein the gN comprises a nucleotide sequence set forth in any one of SEQ ID NOs:5 to 35.

6. The CRISPR-GNDM system according to claim 1, wherein the gN comprises a nucleotide sequence set forth in any one of SEQ ID NOs:9 to 35.

7. A method of treating a disease associated with MYD88 activation in a subject, comprising suppressing MYD88 expression in the subject by targeting an expression regulatory region of MYD88 gene using a CRISPR-GNDM system.

8. The method according to claim 7, wherein the MYD88 expression is suppressed without affecting the expression of an adjacent ACAA1 gene.

9. The method according to claim 7, wherein the disease is selected from the group consisting of an inflammatory disease, an autoimmune disease, an infectious disease and a cancer.

10. The method according to claim 7, wherein the disease is NASH.

11. The method according to claim 7, wherein the disease is a hematological malignancy.

12. The method according to claim 7, wherein the CRISPR-GNDM system comprises (a) a protein selected from the group consisting of dCas9 or dCpf1, and a fusion protein of dCas9 or dCpf1 and Kruppel associated box (KRAB) or other transcription repressor, and (b) a guide nucleotide (gN) targeting an expression regulatory region of MYD88 gene.

13. The method according to claim 12, wherein the protein of (a) is selected from the group consisting of dCas9 or dCpf1, and a fusion protein of dCas9 or dCpf1 and Kruppel associated box (KRAB).

14. The method according to claim 12, wherein the expression regulatory region is a region having the nucleotide sequence set forth in SEQ ID NO: 65.

15. The method according to claim 12, wherein the expression regulatory region is a region having the nucleotide sequence set forth in positions 1,405-7,352 of SEQ ID NO: 65.

16. The method according to claim 12, wherein the gN comprises a nucleotide sequence set forth in any one of SEQ ID NOs:5 to 35.

17. The method according to claim 12, wherein the gN comprises a nucleotide sequence set forth in any one of SEQ ID NOs:9 to 35.

* * * * *